United States Patent
Andersson et al.

(10) Patent No.: US 11,943,588 B2
(45) Date of Patent: Mar. 26, 2024

(54) INTRACUTANEOUS IMPLANTATION TECHNIQUES

(71) Applicant: Cochlear Limited, Macquarie University (AU)

(72) Inventors: Marcus Andersson, Mölnlycke (SE); Marcus Vardfjäll, Mölnlycke (SE); Kristian Gunnar Asnes, Mölnlycke (SE)

(73) Assignee: Cochlear Limited, Macquarie University (AU)

( * ) Notice: Subject to any disclaimer, the term of this patent is extended or adjusted under 35 U.S.C. 154(b) by 2339 days.

(21) Appl. No.: 15/253,093

(22) Filed: Aug. 31, 2016

(65) Prior Publication Data

US 2018/0063658 A1   Mar. 1, 2018

(51) Int. Cl.
*H04R 25/00* (2006.01)
*A61F 11/20* (2022.01)

(52) U.S. Cl.
CPC .......... *H04R 25/606* (2013.01); *A61F 11/20* (2022.01); *H04R 25/554* (2013.01); *H04R 2460/13* (2013.01)

(58) Field of Classification Search
CPC ............... H04R 25/606; H04R 25/554; H04R 2460/13; A61F 11/004; A61N 1/0541; A61N 1/36036
USPC ......... 381/326; 600/25; 607/57, 137; 30/337
See application file for complete search history.

(56) References Cited

U.S. PATENT DOCUMENTS

| | | | | |
|---|---|---|---|---|
| 1,139,796 | A * | 5/1915 | Parker | B26B 5/00 30/337 |
| 3,557,775 | A * | 1/1971 | Mahoney | H04R 25/606 600/25 |
| 4,462,402 | A * | 7/1984 | Burgio | A61N 1/0541 606/129 |
| 7,386,143 | B2 | 6/2008 | Easter et al. | |
| 2007/0191673 | A1* | 8/2007 | Ball | H04R 25/606 600/25 |
| 2009/0287038 | A1* | 11/2009 | Parker | H04R 25/606 600/25 |
| 2015/0246234 | A1* | 9/2015 | Hazard | A61N 1/37518 607/137 |
| 2015/0281860 | A1 | 10/2015 | Johansson et al. | |

OTHER PUBLICATIONS

Bento, Ricardo Ferreira, and Anna Carolina de Oliveira Fonseca. "A brief history of mastoidectomy." International archives of otorhinolaryngology vol. 17,2 (2013): 168-78. doi:10.7162/S1809-97772013000200009 (Year: 2013).*
Ochsner, John. "Surgical knife." Texas Heart Institute journal vol. 36,5 (2009): 441-3. (Year: 2009).*
Cochlear Limited, "Cochlear™ Baha® 4 Attract System Surgical Procedure, Surgery Guide," Jan. 2014.

* cited by examiner

*Primary Examiner* — Phylesha Dabney
(74) *Attorney, Agent, or Firm* — Pilloff Passino & Cosenza LLP; Martin J. Cosenza

(57) ABSTRACT

An exemplary method, comprising generating an inductance signal utilizing an external component held against skin of a recipient, and receiving the inductance signal via an implanted inductance coil implanted in the recipient, wherein a layer of skin is located between the inductance coil and a skull a recipient in which the inductance coil is implanted.

28 Claims, 26 Drawing Sheets

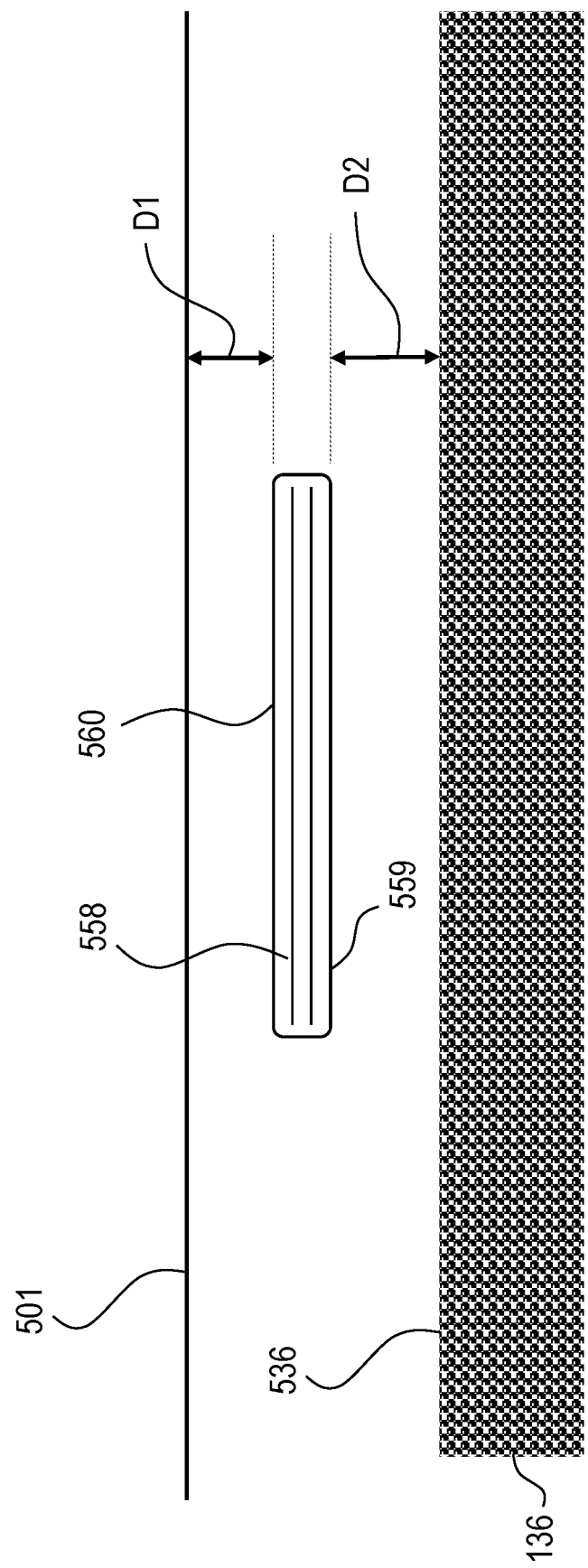

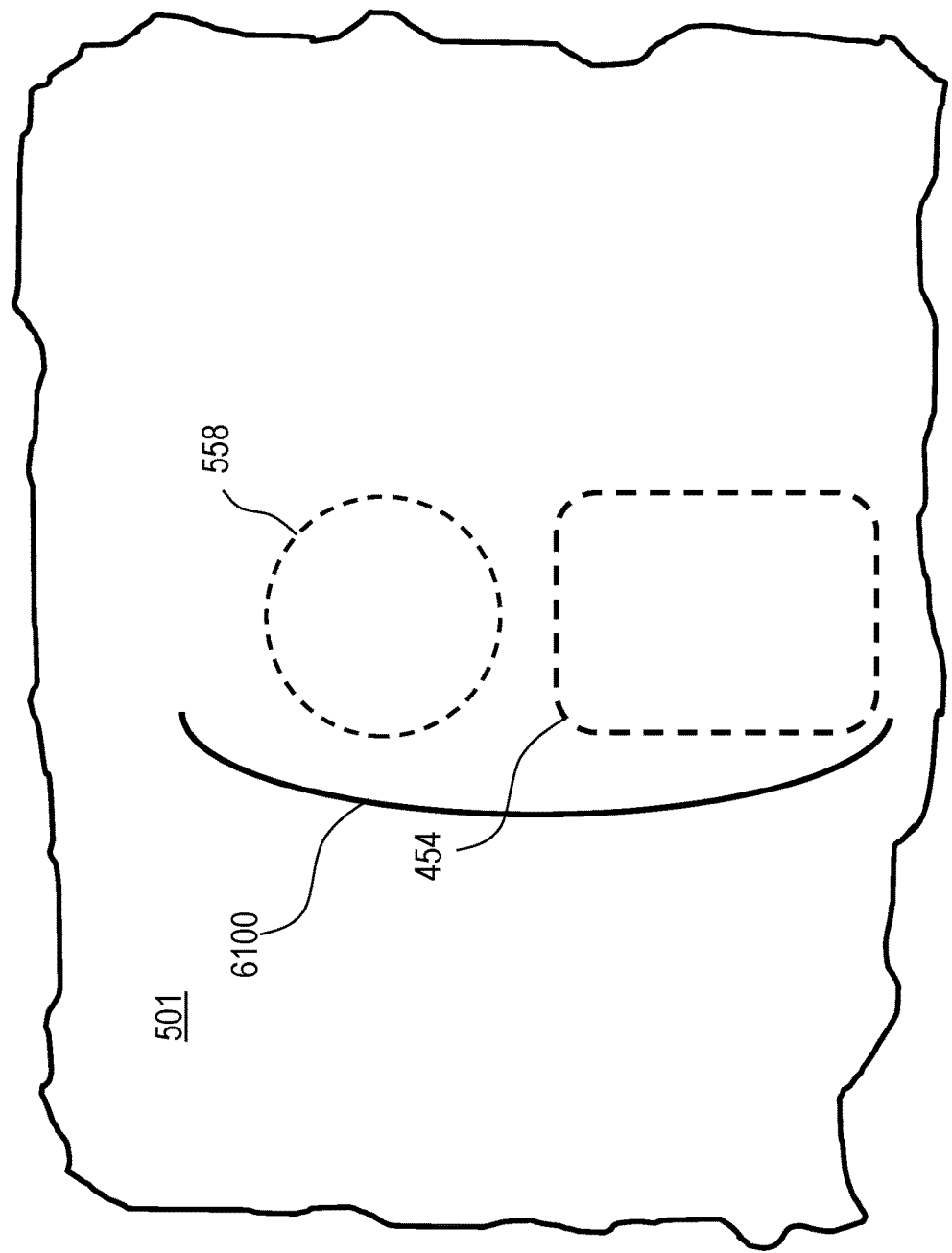

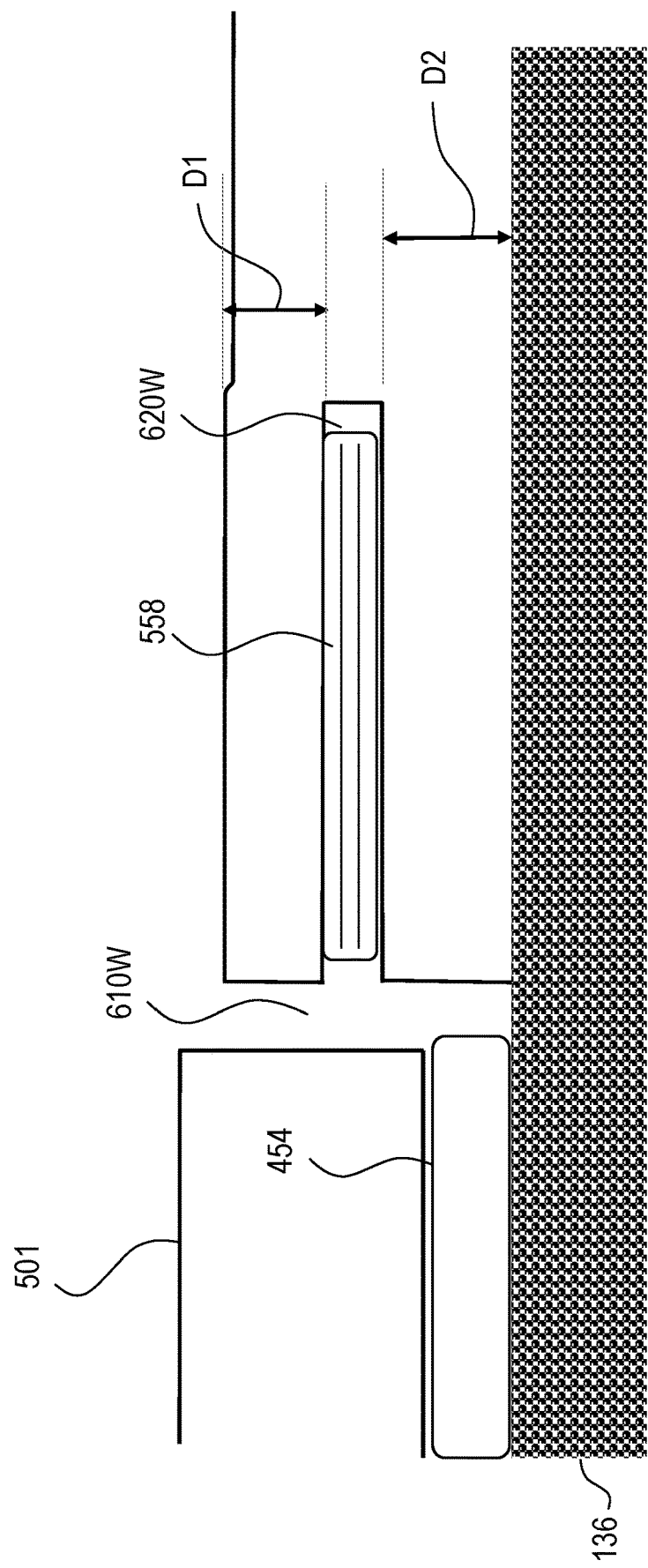

US 11,943,588 B2

INTRACUTANEOUS IMPLANTATION TECHNIQUES

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient to bypass the mechanisms of the ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as bone conduction devices, convert a received sound into vibrations. The vibrations are transferred through the skull to the cochlea causing generation of nerve impulses, which result in the perception of the received sound. Bone conduction devices are suitable to treat a variety of types of hearing loss and may be suitable for individuals who cannot derive sufficient benefit from acoustic hearing aids, cochlear implants, etc., or for individuals who suffer from stuttering problems. Conversely, cochlear implants can have utilitarian value with respect to recipients where all of the inner hair inside the cochlea has been damaged or otherwise destroyed.

SUMMARY

In accordance with one aspect, there is an implant, comprising an assembly, including an electrically conductive inductance circuit supported by a support structure, wherein the assembly is configured to be placed in soft tissue of a human recipient.

In accordance with another aspect, there is a method, comprising cutting into skin of a human recipient above a temporal bone of the recipient; and placing an inductance coil assembly intracutaneously above the mastoid bone through the cut into the skin.

In accordance with another aspect, there is a method, comprising generating an inductance signal external to a recipient; and receiving the inductance signal via an implanted inductance coil implanted in the recipient, wherein a layer of skin is located between the inductance coil and a skull a recipient in which the inductance coil is implanted.

In accordance with another aspect, there is a device, comprising a first portion including first surface, a second portion including a second surface a fixed distance from the first surface, the second surface parallel to the first surface and overlying the first surface when the surfaces are positioned perpendicular to the direction of gravity, wherein the first surface is part of a scalpel blade

BRIEF DESCRIPTION OF THE DRAWINGS

Some embodiments are described below with reference to the attached drawings, in which:

FIG. 5B is a conceptual diagram conceptually illustrating the location of the implanted receiver coil assembly relative to bone 136 and the surface of the skin 501 according to an exemplary embodiment;

FIG. 12 depicts insertion of a plurality of components into respective incisions according to some exemplary embodiments;

DETAILED DESCRIPTION

Figure 1:
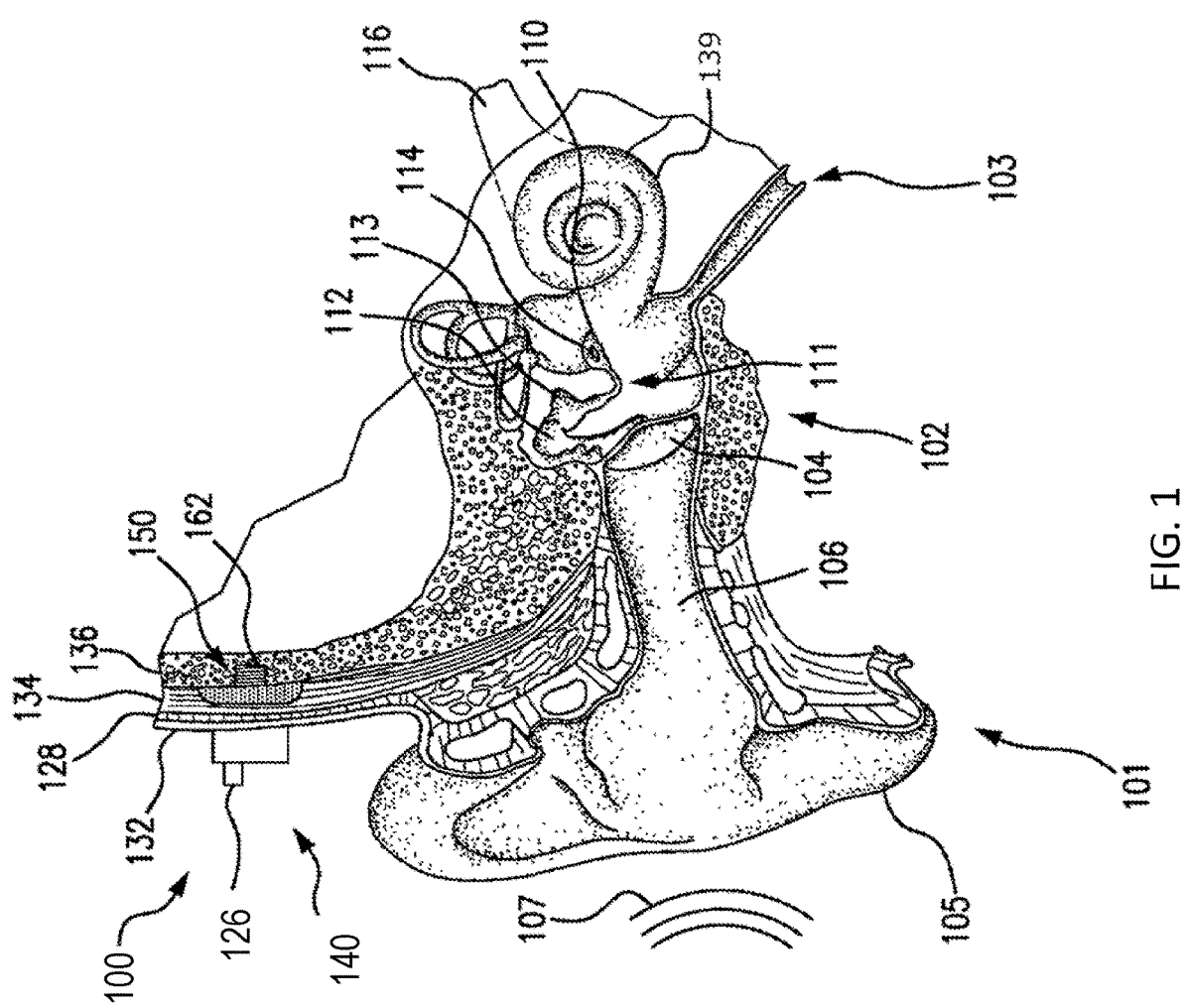
FIG. 1 is a perspective view of an exemplary bone conduction device in which at least some embodiments can be implemented.

Embodiments herein are described primarily in terms of a bone conduction device, such as an active transcutaneous bone conduction device. However, it is noted that the teachings detailed herein and/or variations thereof are also applicable to a cochlear implant and/or a middle ear implant. Accordingly, any disclosure herein of teachings utilized with an active transcutaneous bone conduction device also corresponds to a disclosure of utilizing those teachings with respect to a cochlear implant and utilizing those teachings with respect to a middle ear implant. It is further noted that the teachings detailed herein can be applicable to other types of prostheses, such as by way of example only and not by way of limitation, a retinal implant. Indeed, the teachings detailed herein can be applicable to any component that is held against the body that utilizes an RF coil and/or an inductance coil or any type of communicative coil to communicate with a component implanted in the body. That said, the teachings detailed herein will be directed by way of example only and not by way of limitation towards a component that is held against the head of a recipient for purposes of the establishment of an external component of the hearing prosthesis. In view of this, FIG. 1 is a perspective view of a bone conduction device 100 in which embodiments may be implemented. As shown, the recipient has an outer ear 101, a middle ear 102, and an inner ear 103. Elements of outer ear 101, middle ear 102, and inner ear 103 are described below, followed by a description of bone conduction device 100.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 210 through three bones of middle ear 102, collectively referred to as the ossicles 111 and comprising the malleus 112, the incus 113, and the stapes 114. The ossicles 111 of middle ear 102 serve to filter and amplify acoustic wave 107, causing oval window 210 to vibrate. Such vibration sets up waves of fluid motion within cochlea 139. Such fluid motion, in turn, activates hair cells (not shown) that line the inside of cochlea 139. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102, and inner ear 103 of a recipient of device 100. Bone conduction device 100 comprises an external component 140 and an implantable component 150. As shown, bone conduction device 100 is positioned behind outer ear 101 of the recipient and comprises a sound input element 126 to receive sound signals. Sound input element 126 may comprise, for example, a microphone. In an exemplary embodiment, sound input element 126 may be located, for example, on or in bone conduction device 100, or on a cable extending from bone conduction device 100.

More particularly, sound input device 126 (e.g., a microphone) converts received sound signals into electrical signals. These electrical signals are processed by the sound processor. The sound processor generates control signals which cause the actuator to vibrate. In other words, the actuator converts the electrical signals into mechanical motion to impart vibrations to the recipient's skull.

Alternatively, sound input element 126 may be subcutaneously implanted in the recipient, or positioned in the recipient's ear. Sound input element 126 may also be a component that receives an electronic signal indicative of sound, such as, for example, from an external audio device.

For example, sound input element 126 may receive a sound signal in the form of an electrical signal from an MP3 player electronically connected to sound input element 126.

Bone conduction device 100 comprises a sound processor (not shown), an actuator (also not shown), and/or various other operational components. In operation, the sound processor converts received sounds into electrical signals. These electrical signals are utilized by the sound processor to generate control signals that cause the actuator to vibrate. In other words, the actuator converts the electrical signals into mechanical vibrations for delivery to the recipient's skull.

In accordance with some embodiments, a fixation system 162 may be used to secure implantable component 150 to skull 136. As described below, fixation system 162 may be a bone screw fixed to skull 136, and also attached to implantable component 150.

In one arrangement of FIG. 1, bone conduction device 100 can be a passive transcutaneous bone conduction device. That is, no active components, such as the actuator with electric driver circuitry, are implanted beneath the recipient's skin 132. In such an arrangement, the active actuator is located in external component 140, and implantable component 150 includes a magnetic plate, as will be discussed in greater detail below. The magnetic plate of the implantable component 150 vibrates in response to vibration transmitted through the skin, mechanically and/or via a magnetic field, that is generated by an external magnetic plate.

In another arrangement of FIG. 1, bone conduction device 100 can be an active transcutaneous bone conduction device where at least one active component, such as the actuator with electric driver circuitry, is implanted beneath the recipient's skin 132 and is thus part of the implantable component 150. As described below, in such an arrangement, external component 140 may comprise a sound processor and transmitter, while implantable component 150 may comprise a signal receiver and/or various other electronic circuits/devices.

Figure 2:
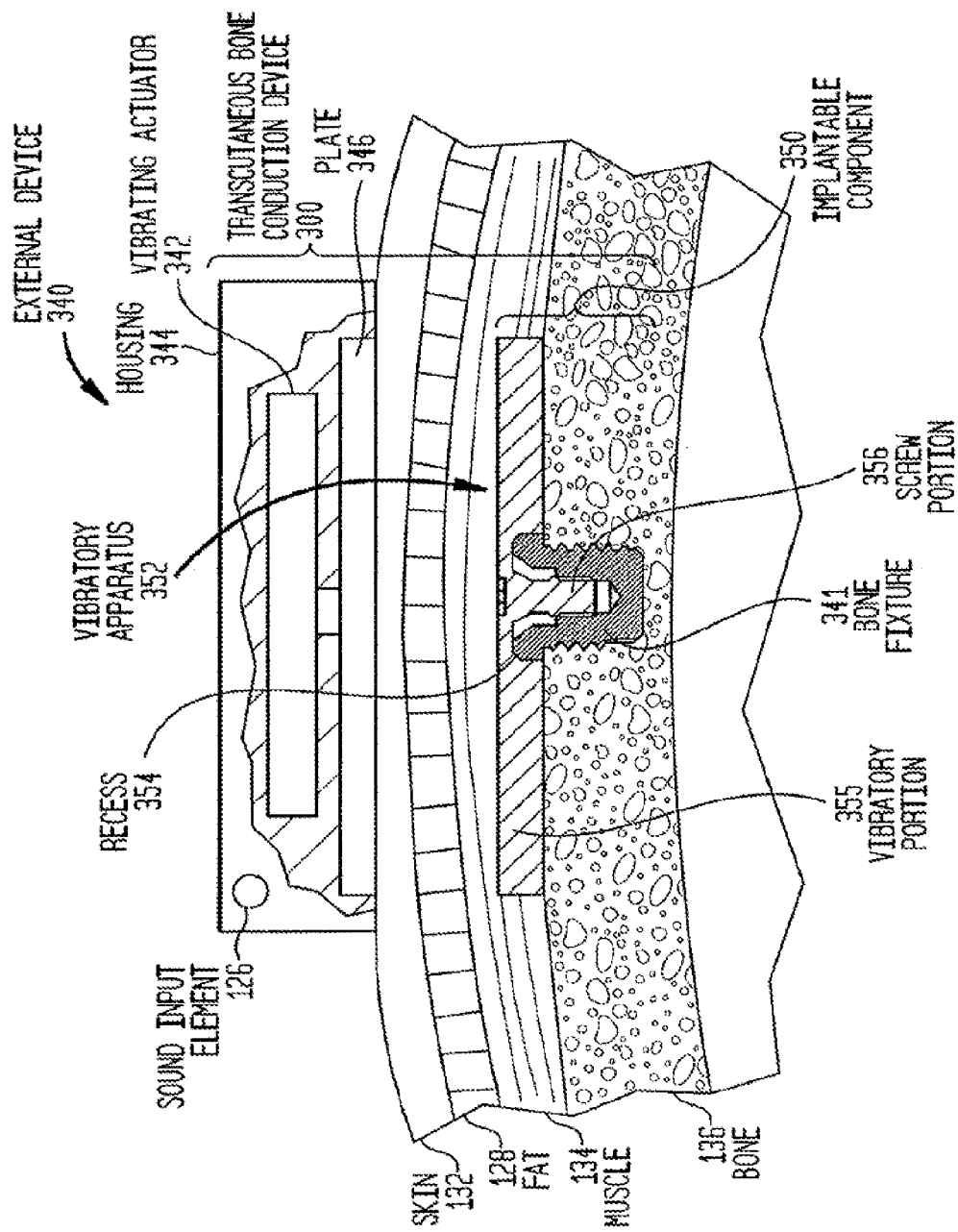
FIG. 2 is a schematic diagram conceptually illustrating a passive transcutaneous bone conduction device.
Figure 3:
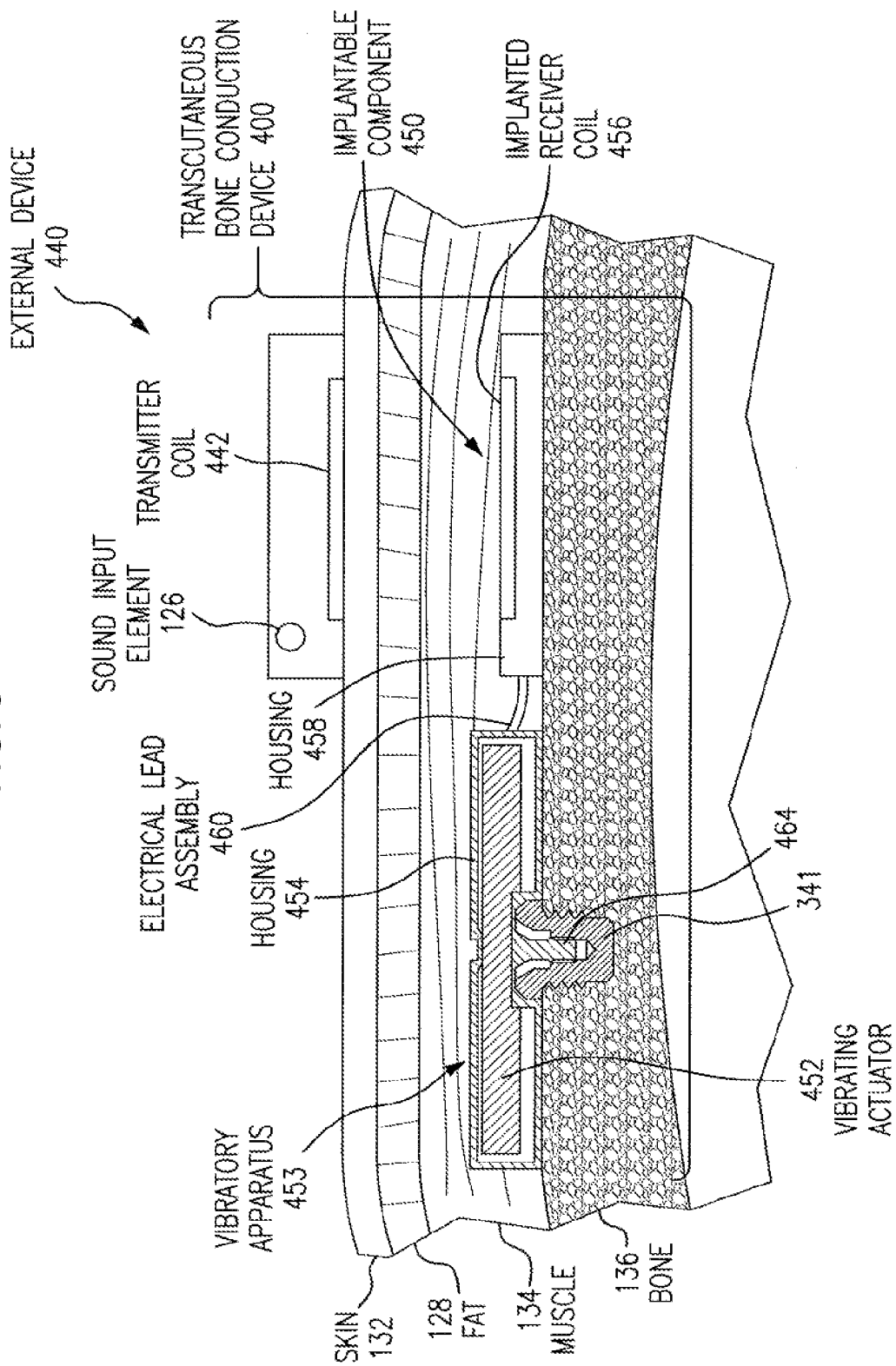
FIG. 3 is a schematic diagram conceptually illustrating an active transcutaneous bone conduction device.

FIG. 2 depicts an exemplary transcutaneous bone conduction device 300 that includes an external device 340 (corresponding to, for example, element 140 of FIG. 1) and an implantable component 350 (corresponding to, for example, element 150 of FIG. 1). The transcutaneous bone conduction device 300 of FIG. 3 is a passive transcutaneous bone conduction device in that a vibrating electromagnetic actuator 342 is located in the external device 340. Vibrating electromagnetic actuator 342 is located in housing 344 of the external component, and is coupled to plate 346. Plate 346 may be in the form of a permanent magnet and/or in another form that generates and/or is reactive to a magnetic field, or otherwise permits the establishment of magnetic attraction between the external device 340 and the implantable component 350 sufficient to hold the external device 340 against the skin of the recipient.

In an exemplary embodiment, the vibrating electromagnetic actuator 342 is a device that converts electrical signals into vibration. In operation, sound input element 126 converts sound into electrical signals. Specifically, the transcutaneous bone conduction device 300 provides these electrical signals to vibrating electromagnetic actuator 342, or to a sound processor (not shown) that processes the electrical signals, and then provides those processed signals to vibrating electromagnetic actuator 342. The vibrating electromagnetic actuator 342 converts the electrical signals (processed or unprocessed) into vibrations. Because vibrating electromagnetic actuator 342 is mechanically coupled to plate 346, the vibrations are transferred from the vibrating electromagnetic actuator 342 to plate 346. Implanted plate assembly 352 is part of the implantable component 350, and is made of a ferromagnetic material that may be in the form of a permanent magnet, that generates and/or is reactive to a magnetic field, or otherwise permits the establishment of a magnetic attraction between the external device 340 and the implantable component 350 sufficient to hold the external device 340 against the skin of the recipient. Accordingly, vibrations produced by the vibrating electromagnetic actuator 342 of the external device 340 are transferred from plate 346 across the skin to plate 355 of plate assembly 352. This can be accomplished as a result of mechanical conduction of the vibrations through the skin, resulting from the external device 340 being in direct contact with the skin and/or from the magnetic field between the two plates. These vibrations are transferred without penetrating the skin with a solid object, such as an abutment, with respect to a percutaneous bone conduction device.

As may be seen, the implanted plate assembly 352 is substantially rigidly attached to a bone fixture 341 in this embodiment. Plate screw 356 is used to secure plate assembly 352 to bone fixture 341. The portions of plate screw 356 that interface with the bone fixture 341 substantially correspond to an abutment screw discussed in some additional detail below, thus permitting plate screw 356 to readily fit into an existing bone fixture used in a percutaneous bone conduction device. In an exemplary embodiment, plate screw 356 is configured so that the same tools and procedures that are used to install and/or remove an abutment screw (described below) from bone fixture 341 can be used to install and/or remove plate screw 356 from the bone fixture 341 (and thus the plate assembly 352).

FIG. 3 depicts an exemplary embodiment of a transcutaneous bone conduction device 400 according to another embodiment that includes an external device 440 (corresponding to, for example, element 140 of FIG. 1) and an implantable component 450 (corresponding to, for example, element 150 of FIG. 1). The transcutaneous bone conduction device 400 of FIG. 3 is an active transcutaneous bone conduction device in that the vibrating electromagnetic actuator 452 is located in the implantable component 450. Specifically, a vibratory element in the form of vibrating electromagnetic actuator 452 is located in housing 454 of the implantable component 450. In an exemplary embodiment, much like the vibrating electromagnetic actuator 342 described above with respect to transcutaneous bone conduction device 300, the vibrating electromagnetic actuator 452 is a device that converts electrical signals into vibration.

External component 440 includes a sound input element 126 that converts sound into electrical signals. Specifically, the transcutaneous bone conduction device 400 provides these electrical signals to vibrating electromagnetic actuator 452, or to a sound processor (not shown) that processes the electrical signals, and then provides those processed signals to the implantable component 450 through the skin of the recipient via a magnetic inductance link. In this regard, a transmitter coil 442 of the external component 440 transmits these signals to implanted receiver coil 456 located in housing 458 of the implantable component 450. Components (not shown) in the housing 458, such as, for example, a signal generator or an implanted sound processor, then generate electrical signals to be delivered to vibrating electromagnetic actuator 452 via electrical lead assembly 460. The vibrating electromagnetic actuator 452 converts the electrical signals into vibrations.

The vibrating electromagnetic actuator 452 is mechanically coupled to the housing 454. Housing 454 and vibrating electromagnetic actuator 452 collectively form a vibratory apparatus 453. The housing 454 is substantially rigidly attached to bone fixture 341.

In an exemplary embodiment, the actuator 452 is a piezoelectric actuator. Any type of actuator that can enable bone conduction hearing can be used in some embodiments.

As can be seen in FIG. 3, the housing 458 of the implanted receiver coil 456 is mounted on the surface of bone 136. In an exemplary embodiment, during implantation of the housing 458, all of the soft tissue above the bone 136 is lifted away from the bone, to form a pocket formed on the top by the soft tissue and on the bottom by the bone 136, and the housing 458 is inserted in the pocket such that the bottom of the housing 458 rests on the top surface of bone 136. Thus, the housing 458 is non-intracutaneously above the bone 136.

Figure 4:
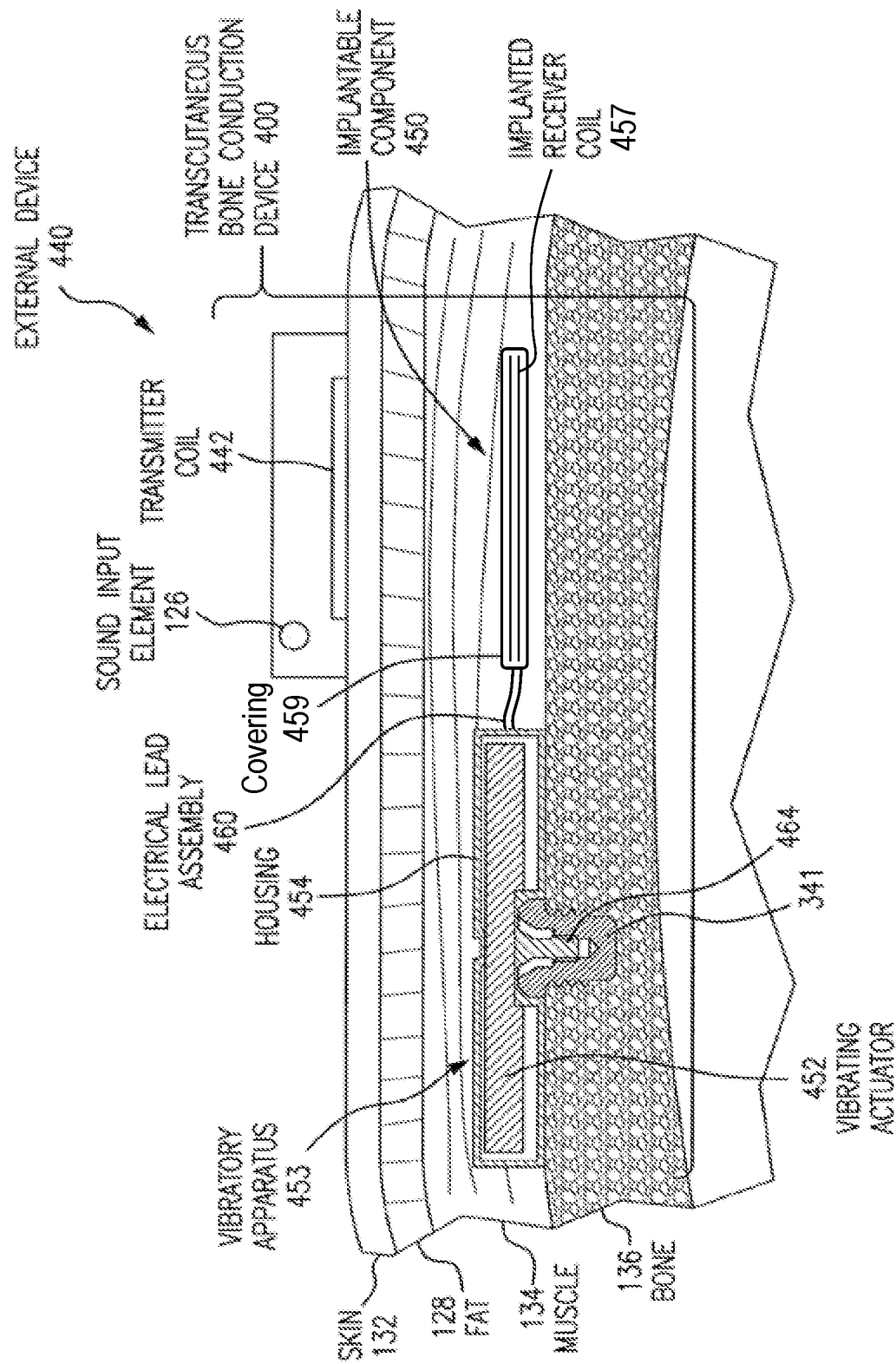
FIG. 4 is a schematic diagram conceptually illustrating an active transcutaneous bone conduction device in accordance with an exemplary embodiment, where the implanted receiver coil 457 is located away from bone 136.

FIG. 4 depicts an alternate embodiment, where the implanted receiver coil 457 is embedded in a silicone cover 459. In this alternate embodiment, the implanted receiver coil 457, or more specifically, the assembly of which the implanted receiver coil 457 is a part (the assembly which includes the silicon covering 459 covering the metallic wires making up the implanted receiver coil 457, the magnet (not shown) and other ancillary components) is located away from the surface of bone 136. In this regard, in the embodiment depicted in FIG. 4, a layer of soft tissue, such as skin, is located between the bottom of the covering 459 of the implanted receiver coil 457 and the surface of bone 136. With respect to the embodiment of FIG. 5A, the receiver coil 457 is located with skin above and below.

FIG. 5B depicts in conceptual terms the position of the implanted receiver coil assembly 558 relative to the outside surface of the skin 501 and the top surface 536 of the bone (e.g., the mastoid bone) 136. More specifically, it can be seen that the bottom surface 559 of the implanted receiver coil assembly 558 is located a distance D2 from the top surface 536 of bone 136. Also, the top surface 560 of the implanted receiver coil assembly 558 is located a distance D1 from the outside surface 501 of the skin/soft tissue above the bone 136. In an exemplary embodiment, the distance D1 is controlled and otherwise set so as to maximize the efficiency of the inductance link between the implanted coil and the external coil. In an exemplary embodiment, D1 is 4 mm. In an exemplary embodiment, D1 can be about 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 2.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or about 6.0 mm or any value or range of values therebetween in 0.01 mm increments (about 3.33 mm, 4.44 mm, 2.54 mm to about 5.14 mm, etc.). D2 can have comparable numbers (D2 need not be the same as D1, D2 can be a number corresponding to one of the aforementioned numbers/can be a range of the aforementioned ranges, etc.).

In an exemplary embodiment, distance D1 is effectively constant over the length of the assembly 558, at least when measured without compression of the skin between the assembly 558 and the surface 501 of the skin (the skin is in a static and unloaded state). In an exemplary embodiment, the respective values of the distance D1 measured at locations along the assembly 558 have differences less than about 0.5 mm, 0.4 mm, 0.3 mm, 0.2 mm, 0.1 mm, or less, or any value or range of values therebetween in about 0.01 mm increments. Such is also the case with respect to D2.

It is noted that FIG. 5B is not drawn to scale. It is also noted that the pockets of the soft tissue in which the implanted receiver coil assembly 558 is located is not shown per se. In the arrangement depicted in FIG. 5B, the soft tissue is conceptually depicted as forming a perfect adherence to the outer surface of the silicon covering of the implanted receiver coil assembly 558. In some embodiments, at least over time, the soft tissue grows around the implanted receiver coil assembly 558 in a manner analogous to that depicted in FIG. 5B. That said, in some alternate embodiments, there will be gaps between the outer surface of the silicon covering of the assembly 558 and the soft tissue. It is also noted that an exemplary embodiment of FIG. 5B corresponds to assembly 558 being placed intradermally in skin of the human recipient. It is also noted that an exemplary embodiment of FIG. 5B corresponds to assembly 558 being placed intracutaneously in the human recipient. Thus, in an exemplary embodiment, skin tissue is located above and below the assembly. In an exemplary embodiment of such embodiment, fat and muscle are located below the layer of skin beneath the assembly.

Figure 5A:
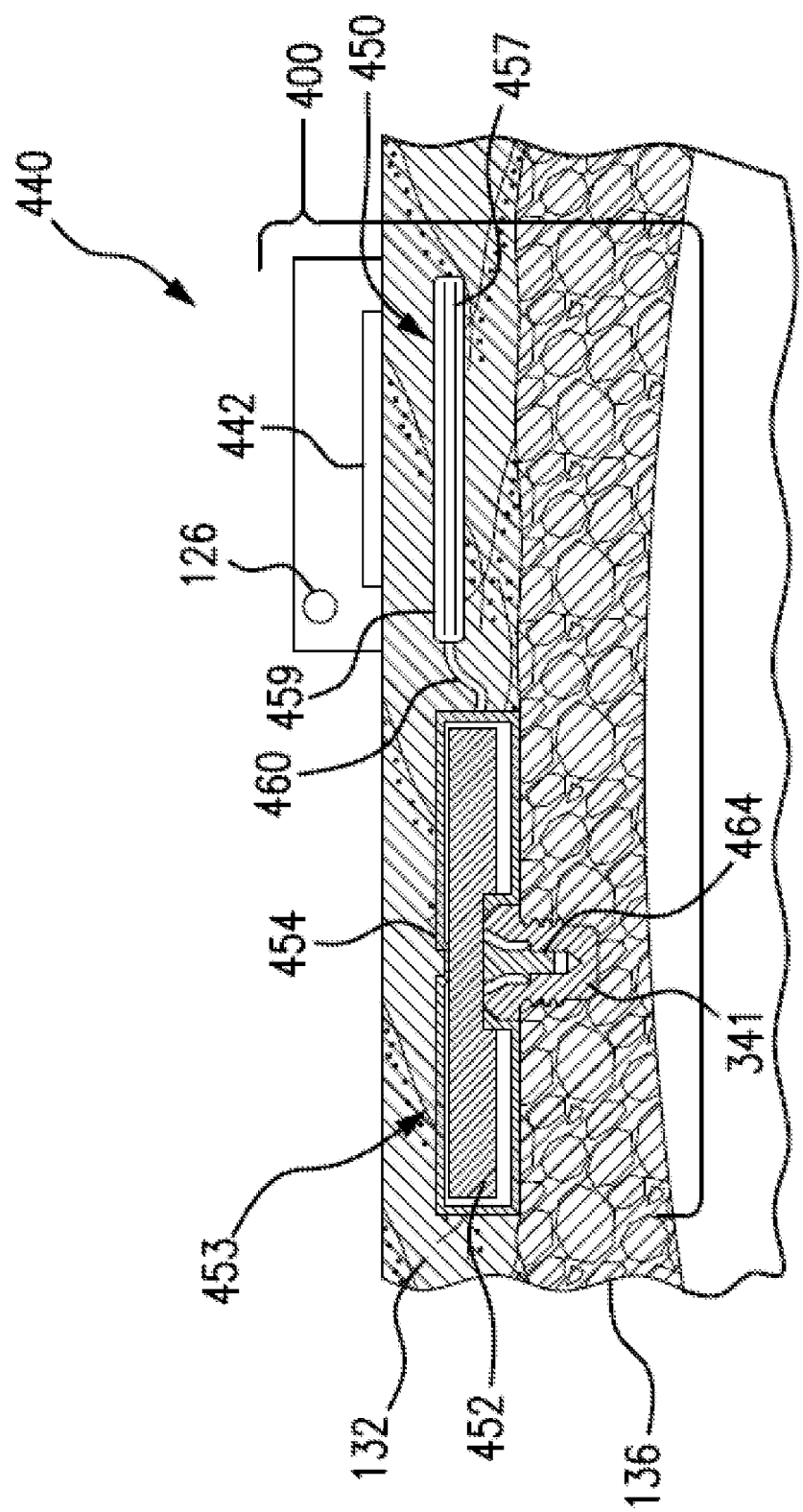
FIG. 5A is a schematic diagram conceptually illustrating an active transcutaneous bone conduction device in accordance with another exemplary embodiment, where the implanted receiver coil 457 is located away from bone 136 entirely within skin.

Accordingly, in view of FIGS. 4 and 5A and 5B, in an exemplary embodiment, there is an implant, comprising an assembly, such as implanted receiver coil assembly 558, that includes an electrically conductive inductance circuit, such as implanted receiver coil 457, supported by a support structure, such as covering 459, which, as noted above, can be made of silicone, or any other appropriate material, wherein the assembly is configured to placed in soft tissue of the human (where "in soft tissue" means that the soft tissue is located above and below the assembly)—here, between muscle, but in other embodiments, can be placed between skin or fat (separately or in combination, with skin on top and fat on the bottom), between fat or muscle (again, separately or in combination). This as opposed to the embodiment depicted in FIG. 3, where the assembly including the implanted receiver coil 456 is located completely beneath the skin, completely beneath the soft tissue/where the assembly including the implanted receiver coil 456 is located directly against the bone 136.

In an exemplary embodiment, the electrically conductive circuit is a coiled wire of an inductance coil configured to establish an inductance link with an external inductance coil.

It is noted that while the embodiments depicted above have focused on a coiled wire establishing the implanted receiver coil 457, in an alternate embodiment, conductive traces on a PCB can be utilized as an inductive receiver component. In this regard, the phrase inductance coil as used herein includes both wired coils and conductive traces and any other structure that can enable inductance communication with an external inductance coil/an external inductance field.

Note also that while the embodiments detailed herein generally focus on an inductance coil embedded in a silicon body, the teachings detailed herein are applicable to other arrangements, such as inductance coils located in a titanium housing or a plastic housing, etc., where the housings are located in the recipient respect to the surface of the bone 136 according to the teachings detailed herein.

Still further, as can be understood from the above, in an exemplary embodiment, the assembly 558 is implanted in the recipient such that there is between about 2 mm and about 5 mm of skin above the assembly and at least about 1 mm of skin below the assembly.

As noted above, the implanted receiver coil assembly 558 in general, and the receiver coil 457 thereof in particular, is in signal communication with one or more components located in the housing 452 of the vibratory apparatus 453. In this regard, as noted above, a vibrating actuator 452 can be located in the housing numeral 454. Accordingly, the housing 454 can include an active component of a hearing prosthesis located in a housing remote from the implanted receiver coil assembly 558. In an exemplary embodiment, the receiver coil 457 generates a current that is supplied to the actuator and thus powers the actuator and controls the actuator to actuatoe so as to generate vibrations to evoke a bone conduction hearing percept. In an exemplary embodiment, the implanted receiver coil assembly 558 in general, and the receiver coil 457 thereof in particular, is in signal communication with the actuator 452 via electrical lead assembly 460. In an exemplary embodiment, electrical lead assembly 460 extends to feedthroughs of the housing 454, which feedthroughs are in turn in signal communication with the actuator 452.

While the embodiment of FIG. 4 discloses an electromagnetic actuator as the active component of the hearing prosthesis, which active component is in signal communication with the implanted receiver coil 457, in an alternate embodiment, the active component can be a piezoelectric actuator. Accordingly, in an exemplary embodiment, the active component can correspond to any type of electrode—mechanical actuator/transducer. Still further, while the embodiments detailed above have been directed towards an active transcutaneous bone conduction device, in an alternate embodiment, the implanted receiver coil 457 can be in signal communication with an actuator of a middle ear implant, which actuator can correspond to the active component of the hearing prosthesis.

Also, the implanted receiver coil 457 can be in signal communication with a stimulator of a cochlear implant, which stimulator corresponds to the active component of the hearing prosthesis. It is noted that the stimulator can correspond to an active component that is located in a housing, even though the electrodes to which current is provided from the stimulator located outside the housing. In this regard, the output of the active component is output from the housing via an electrical route in a manner analogous to how the vibrations are outputted from the housing via a mechanical route.

In view of the above, in an exemplary embodiment, the implant includes electro-mechanical transducer located in a housing remote from the implanted receiver coil assembly 558, wherein the implanted receiver coil assembly 558 is in signal communication with at least one component located in the housing via a lead extending from the assembly 558 to the housing.

Figure 6:
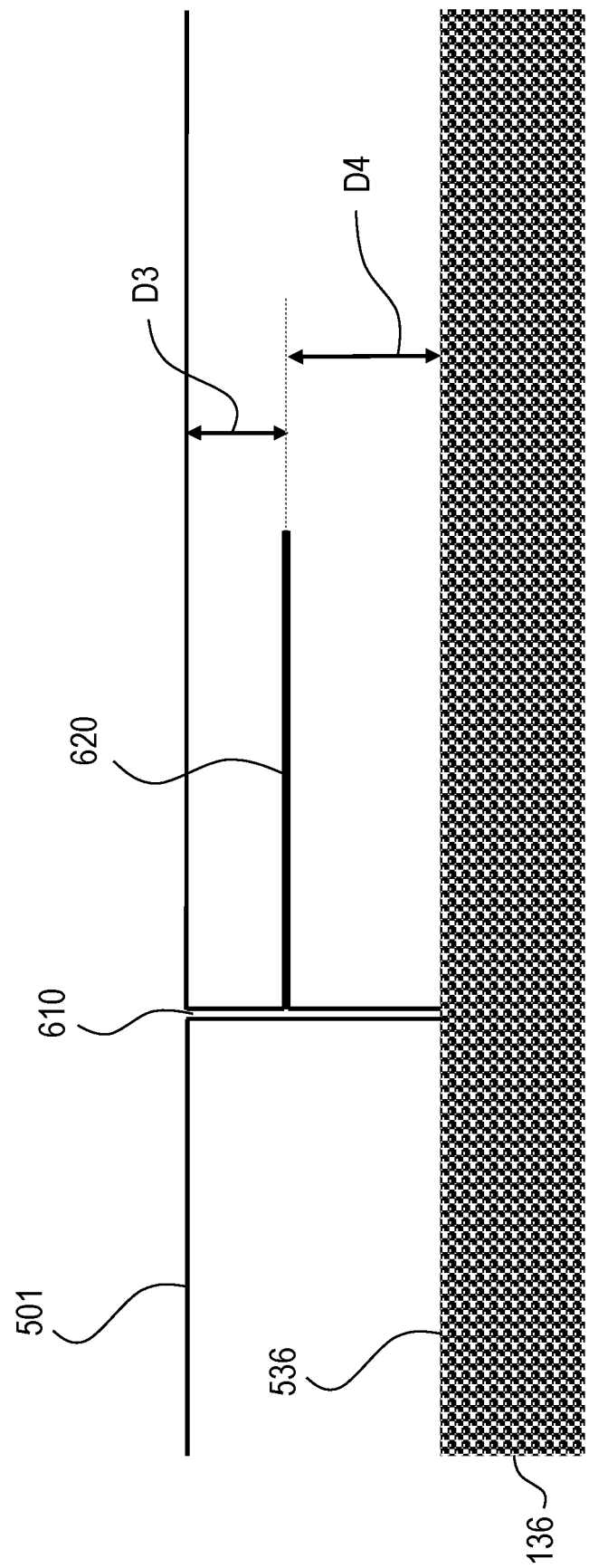
FIGS. 6 to 7 depict exemplary incisions according to some exemplary embodiments.

FIG. 6 depicts an exemplary set of incisions in skin of the recipient (the area above the surface 536 of bone 136) applicable to an exemplary method of implanting the assembly 558 and the associated remote housing with the active component therein. In particular, there is a first incision 610, which is made from the outer surface of the skin 501 down to the surface 536 of bone 136 or, in some other embodiments, down to the periosteum. In some embodiment, a separate incision into the periosteum is made subsequent to the formation of incision 610, which collectively forms incision 610, while in other embodiments, the periosteum is cut separately after a skin flap is pulled away from the incision 610 (more on this below). Incision 610 is typically, but need not be, normal to the tangent line of the surface 536 of bone 136. Incision 610 is typically, but need not necessarily be, an incision that goes all the way, or at least substantially all the way to the surface 536 of bone 136 or the periosteum. Such can have utilitarian value with respect to implanting the housing containing active component directly against bone 136, as will be described in greater detail below. That said, in some alternate embodiments, the incision 610 is made in a manner that is not extend all the way to the surface 536 of the bone or to the periosteum. Indeed, with respect to the features of the implanted receiver coil assembly 558, incision 610 need only be, in at least some exemplary embodiments, to the depth of incision 620, or slightly below the depth of incision 620, where incision 620 formed the pocket for the receiver coil assembly 558. With respect to the incision 620, incision 620 is an incision that is made parallel to the surface 501 of the skin. In an exemplary embodiment, the parallel features of the incision 620 correspond to the tangent of the surface 501 of the skin immediately above the device utilized to cut the pocket 620 (e.g., the edge and/or tip of a scalpel—such will be described in greater detail below). In an exemplary embodiment, the distance that incision 620 extends from incision 610 is about 30 mm, which is about or slightly more than the outer diameter of the implanted receiver coil assembly 558. In an exemplary embodiment, the distance that the incision 620 extends from incision 610 is about 35 mm. That said, owing to the features of the teachings detailed herein these of the placement of the receiver coil 457 a fixed distance from the surface 501 of the skin, in some embodiments, the outer diameter of the implanted receiver coil 457 can be lower than that which would otherwise be the case owing to the increased efficiency achieved by placing the receiver coil 457 as detailed herein, and thus the outer diameter of the implanted receiver coil assembly 558 can be smaller than that which would otherwise be the case. Accordingly, in an exemplary embodiment, the distance that the incision 620 extends from incision 610 can be about 15 mm or 20 mm or 25 mm or 30 mm or 35 mm or 40 mm or more or any value or range of values therebetween in 1 mm increments, depending on the diameter of the coil assembly.

FIG. 6 depicts distance D3 and distance D4. Distance D3 corresponds to the distance from the incision 610 to the local surface of the skin (the portion immediately above by way of the direction normal to the tangent line of the incision). In an exemplary embodiment, distance D3 is effectively constant over the length of the incision 610, at least when measured without compression of the skin between the incision 610 and the surface 501 of the skin (the skin is in a static and unloaded state). In an exemplary embodiment, the respective values of the distance D3 measured at locations along the incision 610 have differences less than about 0.5 mm, 0.4 mm, 0.3 mm, 0.2 mm, 0.1 mm or less or any value or range of values therebetween in about 0.01 mm increments. Such can also be the case with respect to D4. In an exemplary embodiment, D3 is 4 mm. In an exemplary embodiment, D3 can be about 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 2.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or about 6.0 mm or any value or range of values therebetween in 0.01 mm increments (about 3.33 mm, 4.44 mm, 2.54 mm to about 5.14 mm, etc.).

D4 can have comparable numbers (D4 need not be the same as D3, D4 can be a number corresponding to one of the aforementioned numbers/can be a range of the aforementioned ranges, etc.).

A tool having utilitarian value with respect to creating incision 610 achieving the aforementioned values will be described in greater detail below.

Figure 7:
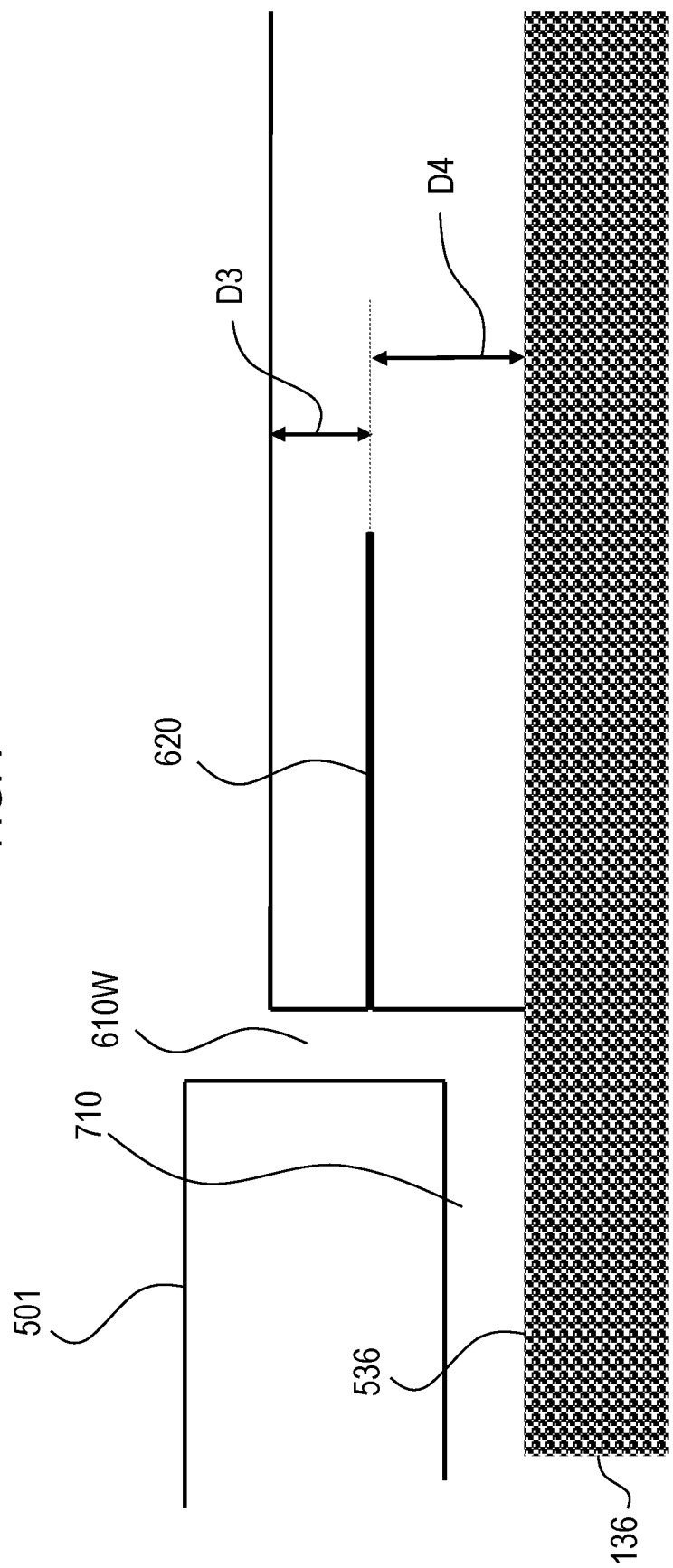

Still with reference to the figures, FIG. 7 depicts how incision 610 is widened to create widened incision 610W. In this regard, because of the elastic nature of skin, the incision 610 can be the basis for the widened incision by simply pushing the walls (the vertical walls) of the incision away from each other. Still further, as can be seen in FIG. 7, a space 710 is opened between the skin and the bone 136 in general, and the surface 536 of the bone in particular. This can be done utilizing a scalpel to detach the skin from the bone 536, or by utilizing any other method (e.g., the skin may be pulled away from the surface of the bone 536 using one hand, and some embodiments).

Figure 8:
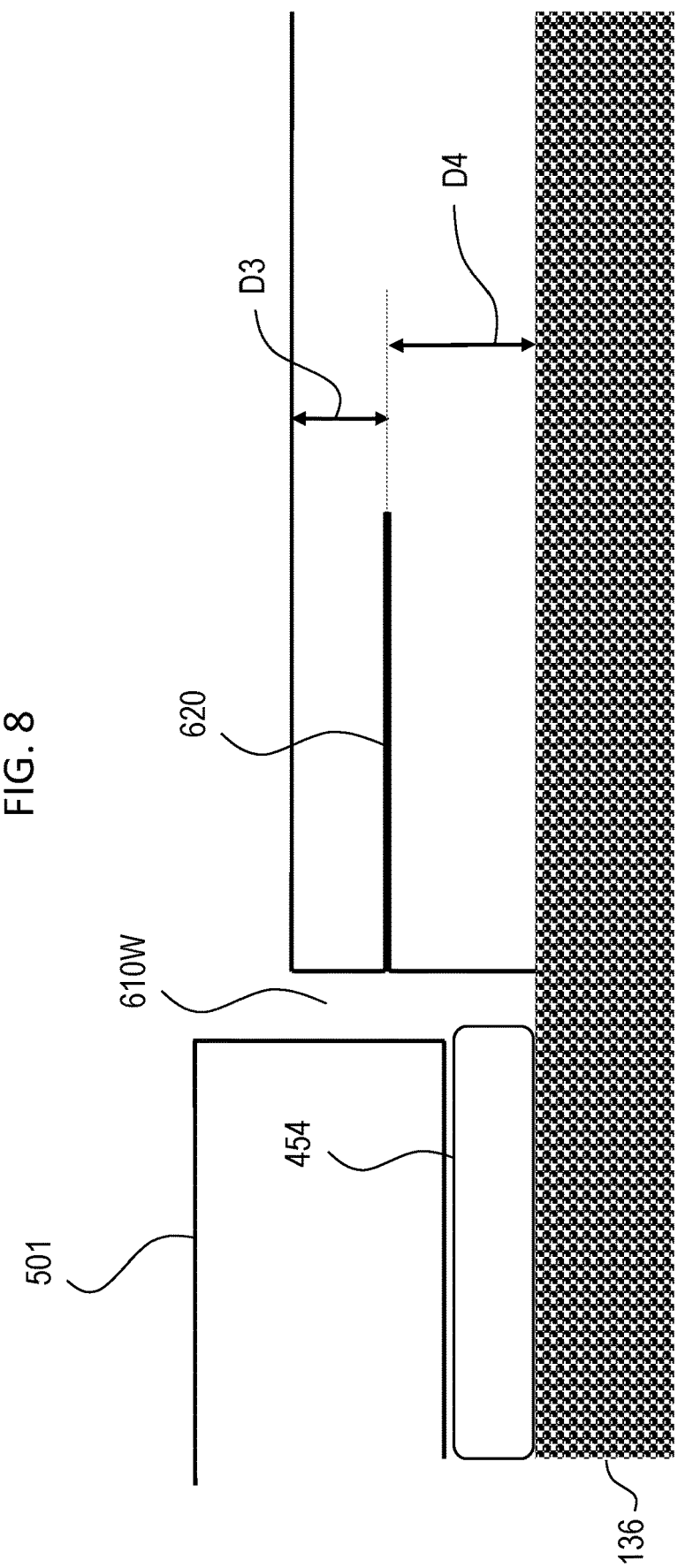
FIG. 8 depicts insertion a component of the implant into the incisions according to some exemplary embodiments.

Space 710 is established so as to make room for the housing 454. In this regard, FIG. 8 depicts housing 454 being placed into space 710. It is noted that the lead associated with the implantable component is not shown for purposes of clarity. In at least some exemplary embodiments, the lead will extend through the widened incision 610W to the implanted receiver coil assembly 558.

Figure 9:
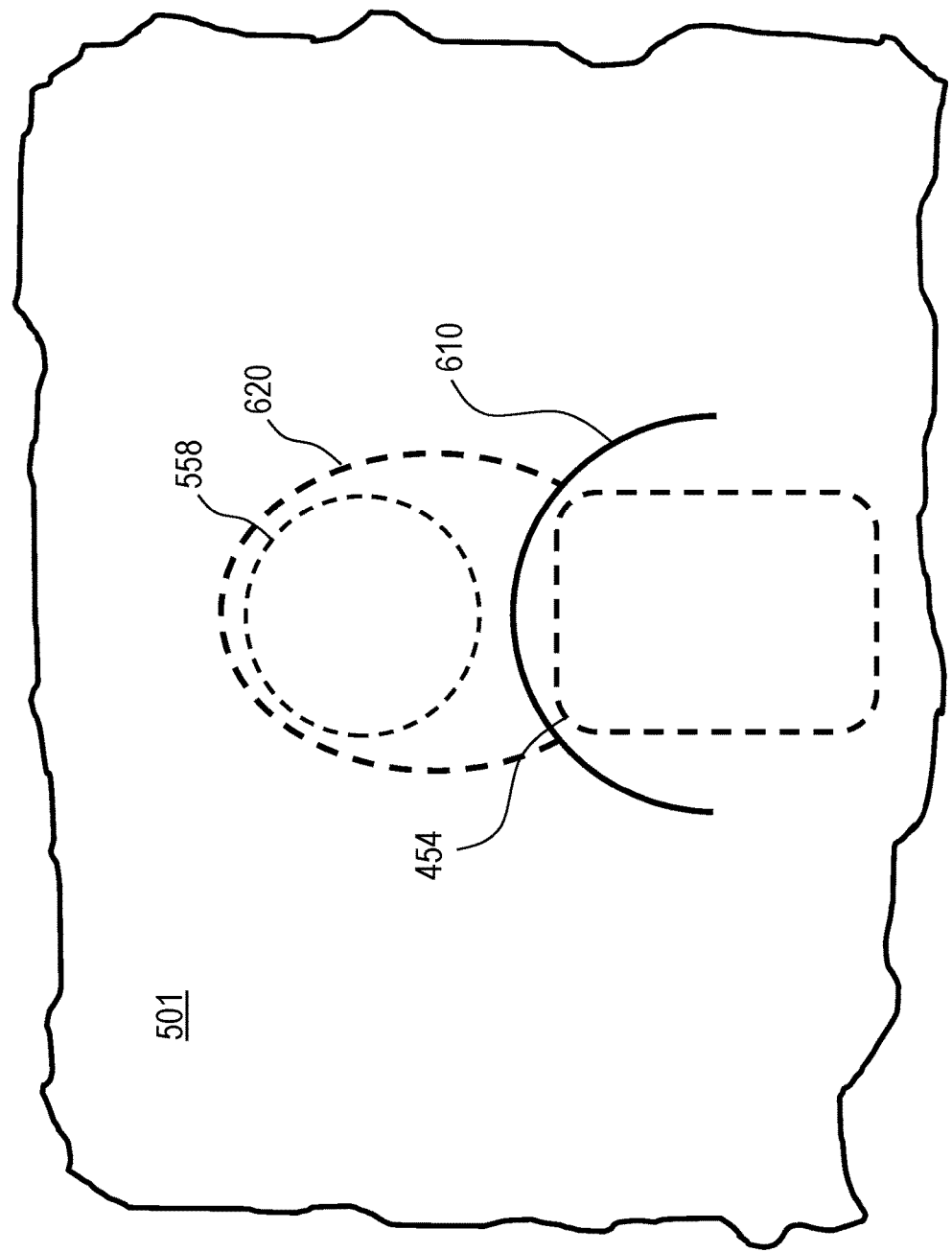
FIGS. 9-11B depicts a view looking downward onto the skin, with incisions in the skin and components of the implant implanted in the skin according to some exemplary embodiments.

It is noted that incision 610 can be created in an arcuate manner/semicircle manner, when viewed looking downward onto the surface of the recipient's skin. FIG. 9 depicts an exemplary conception schematic looking downward onto skin 501 from the outside of the recipient. As can be seen, incision 610 is an arcuate shape. Incision 610 is typically created so as to provide space for the housing 454 to be inserted therein, which housing 454 is depicted in—lines for purposes of conceptual visualization. Incision 620 is also depicted in dashed lines, where the area inside the dashed line 620 bounded by the incision 610 forms the pocket for the implanted receiver coil assembly 558.

Figure 10:
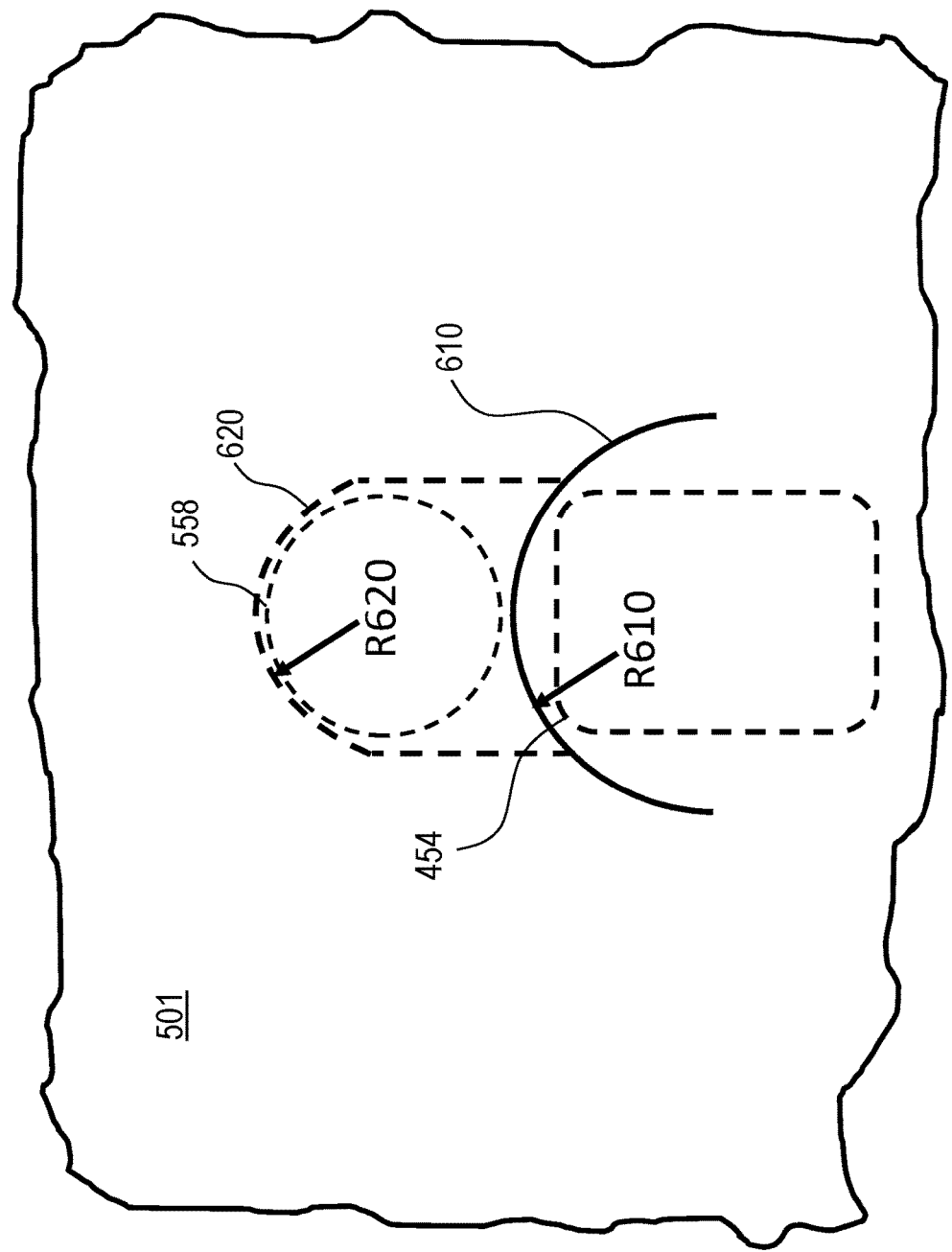

FIG. 10 depicts a slightly more precise set of incisions, where instead of a pocket for incision 620 having curved surfaces all around, only a portion of the outer boundary of the pocket formed by incision 620 is curved. In this regard, the curved section has a radius R620 which corresponds to the radius R610 of incision 610. In this regard, as will be detailed below, in an exemplary embodiment, the flap established by incision 610 is pulled backwards (thus, in some embodiments, establishing incision 610W, where the skin on the outside of the curve remains in place. A scalpel having a defined length is inserted into the skin to establish incision 620 at a location at the apex of the curve 610 until a stop on the scalpel reaches the skin established on the outer curvature of incision 610W. The scalpel is then moved sideways (left or right with respect to the frame of reference of FIG. 10) such that the outer surface of incision 610W "pushes" the stop downward (with respect to the frame of reference of FIG. 10), and thus pulls the distance of insertion of the scalpel downwards, thereby forming the curve R620 corresponding to curve 610. The scalpel is moved sideways until a distance of about half the diameter of the implanted receiver coil assembly 558 is opened up (a distance in the horizontal direction). The process is repeated for the other direction, thus establishing pocket 620.

Again, some additional details of the utilization of the tool to achieve the formation of the pocket 620 will be described in greater detail below.

Figure 11A:
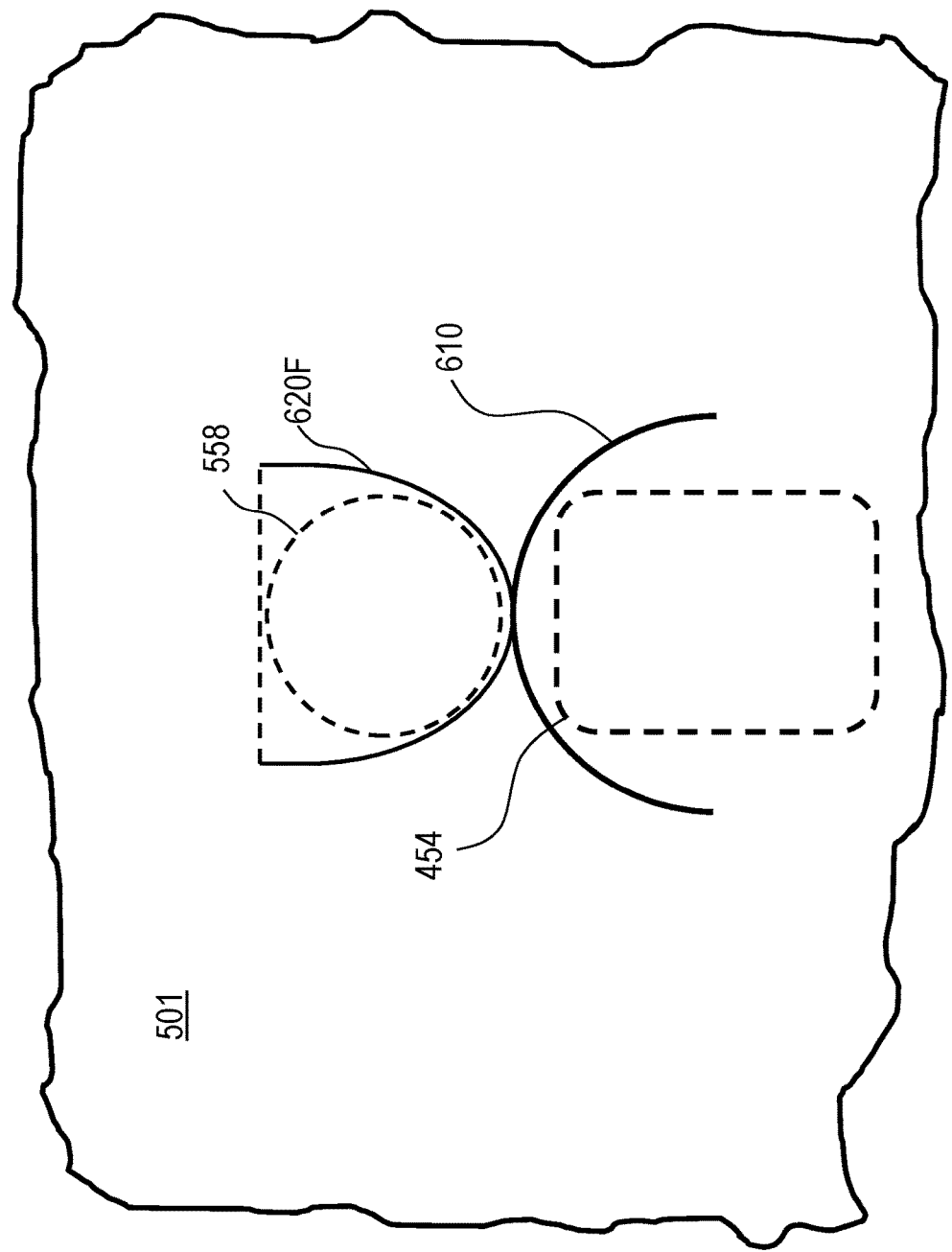

The embodiment of FIG. 10 and FIG. 9 for this matter, are embodiments where a skin flap is not created with respect to the pocket 620. This is as opposed to the skin flap created by the incision 610 vis-à-vis the locations of the skin inside the curve. That is, the incision establishing the pocket are entirely intradermal and do not rise to the level of the surface of the skin 501 (hence the outline of the pocket is depicted in dashed lines in the FIGS. of 9 and 10, as it is entirely below the surface of the skin, save for the common boundary of incision 610). FIG. 11A, however, depicts an alternate incision regime into the skin of the recipient where a skin flap is formed in a manner analogous to that formed by incision 610 for insertion of the housing 454. More particularly, incision 620F (for flap) is created in the surface 501 of the skin, as is represented by the solid lines. In an exemplary embodiment, this flap is back (upwards, with respect to the frame of reference of FIG. 11A), and hinged along the dashed line portion of the incision 620F, so that the implanted receiver coil assembly 558 can be placed onto the bed of skin overlying the bone. In such placement, the skin flap is put back in place, and the boundary of the incision at the surface of the skin 501 is sutured (or any other process of closing the incision can be utilized). FIG. 11B depicts an alternate incision regime, where the incision 6100 is on the side of both element 558 and element 454. Note also that in some embodiments, the incision 6100 may not extend the full longitudinal length of both elements, but could extend a portion, of the length, and then, under the surface of the skin, dog leg to make room for the component(s).

In any event, FIG. 12 depicts an exemplary placement of the implanted receiver coil assembly 558 into a widened pocket 620W (widened from that resulting from the incision, due to the placement of the receiver coil assembly 558 therein). In this embodiment, the incision 610W is shown in its widened state as well. It is noted that after the procedure, the width of the incision 610W will be reduced for closure.

Figure 13:
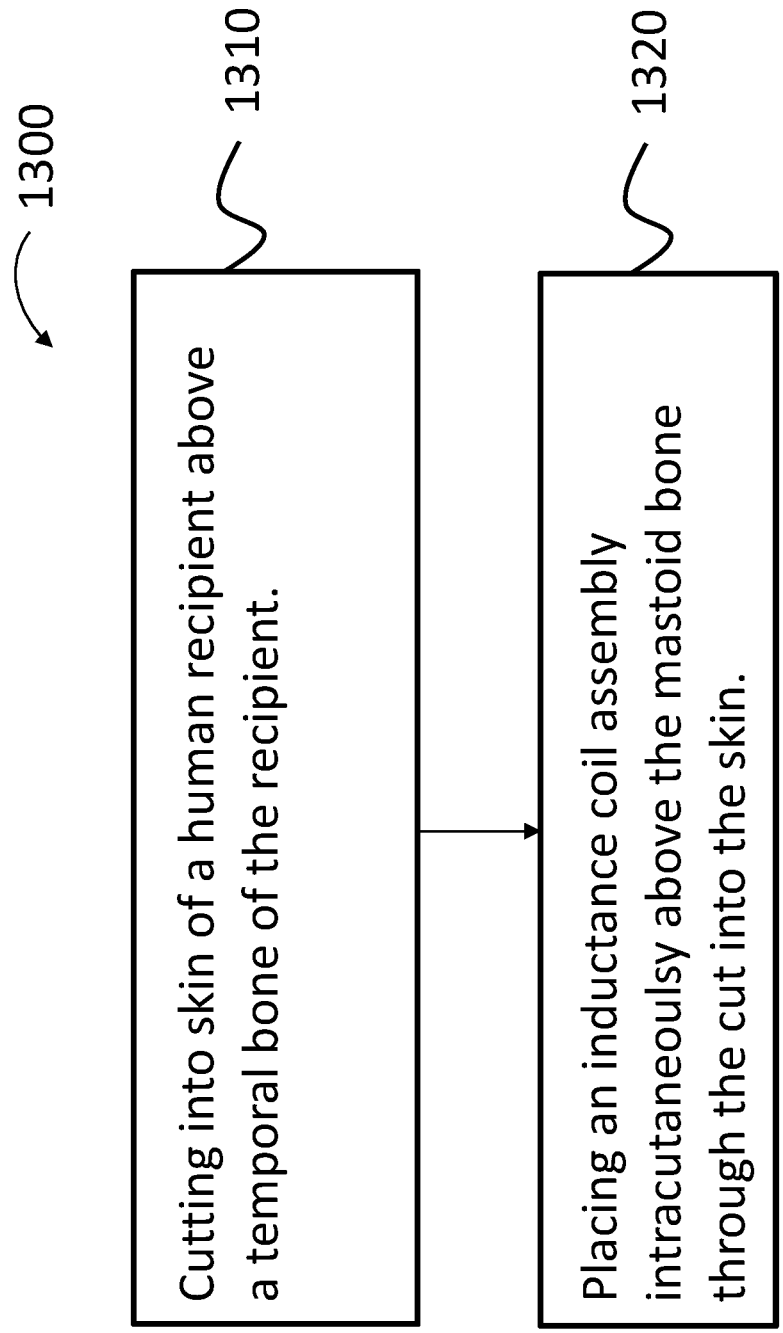
FIGS. 13-15 represent flowcharts according to exemplary methods according to some exemplary embodiments.

In view of the above, some exemplary methods according to the teachings detailed herein will now be detailed. FIG. 13 depicts an exemplary flowchart for an exemplary method 1300. Method 1300 includes method action 1310, which includes the action of cutting into skin of a human recipient above a temporal bone of the recipient. By way of example only and not by way of limitation, such action can correspond to the action executed to create the pocket 620 detailed above. Method 1300 further includes method action 1320, which includes placing an inductance coil, such as by way of example only and not by way of limitation, the implanted receiver coil detailed above, intracutaneously above the mastoid bone through the cut into the skin. Because the method action 1320 includes placing the coil intracutaneously, there will be a layer of skin between the mastoid bone and the coil (there will also be a layer of silicon between the coil in the mastoid bone in embodiments that utilize silicon as the covering for the coil). Accordingly, method action 1320 results in a placement of the coil where the coil is separated from the outer surface of the bone (i.e., the surface facing external to the human) and separated from the outer surface of the periosteum covering the bone.

In an exemplary embodiment of method 1300, method action 1320 results in the inductance coil assembly being located such that there is between about 2 mm and about 5 mm of skin above the inductance coil assembly and at least about 1 mm of skin below the inductance coil assembly. Still further, in an exemplary embodiment of method 1300, method action 1220 results in the inductance coil assembly being located such that there is between about 3.5 mm and about 4.5 mm of skin above the inductance coil assembly in at least about 1 mm of skin below the inductance coil assembly. It is also noted that in some alternate embodiments, other dimensions are present, such as those detailed above by way of example only and not by way of limitation.

Still further consistent with the teachings above with regard to the formation of the pocket, in an exemplary embodiment, the action of cutting into the skin of the recipient executed in method action 1310 includes cutting a pocket into the skin, the pocket having a width and a length that extends at least generally parallel to a surface of the mastoid bone above the recipient. As also detailed above, in an exemplary embodiment, the pocket has a width and length that extends at least generally parallel to a surface of the skin.

Figure 14:
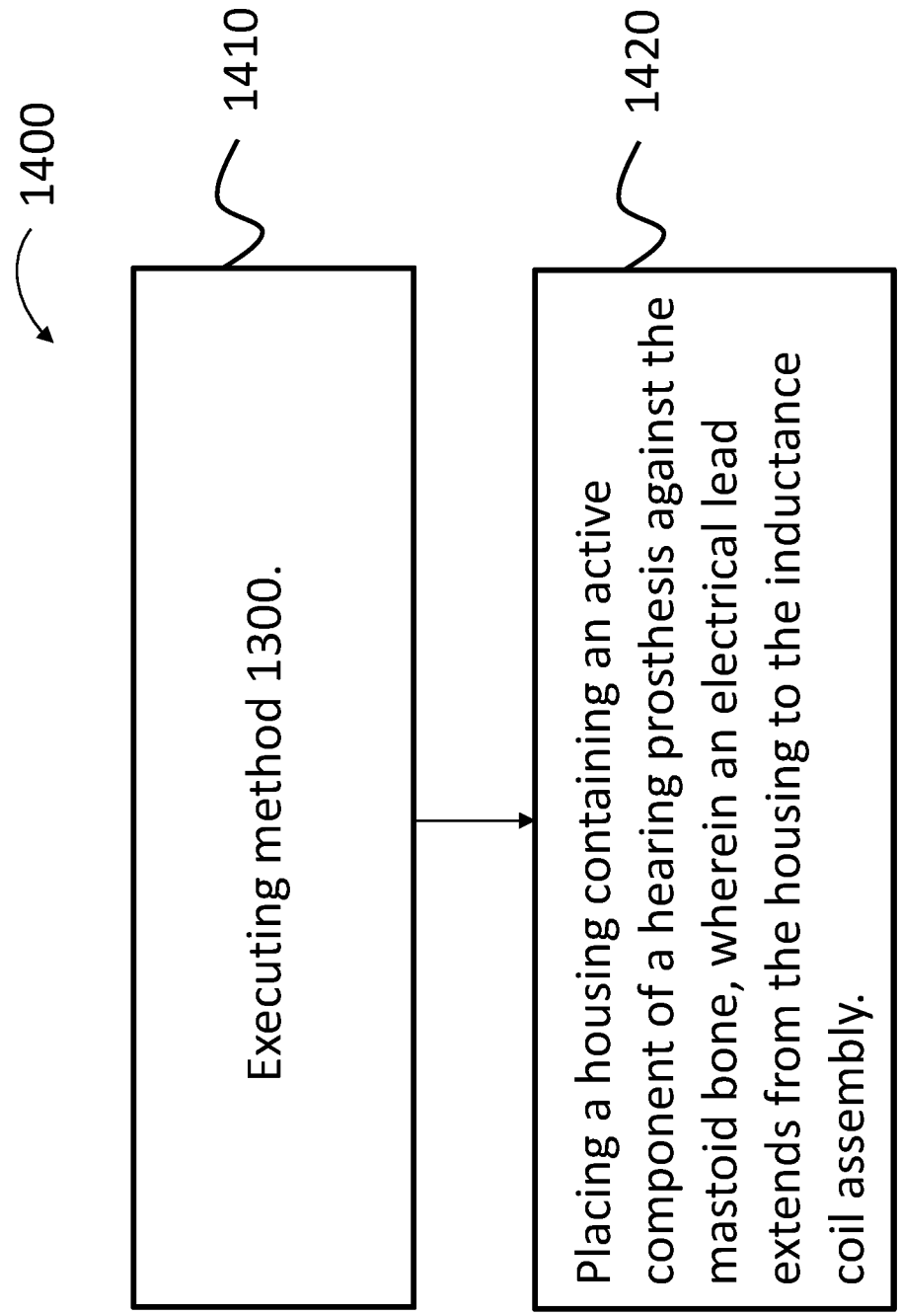

FIG. 14 presents another exemplary flowchart according to another exemplary method, method 1400, according to an exemplary embodiment. Method 1400 includes method action 1410, which includes executing method 1300. Method 1400 further includes method action 1420, which includes placing a housing containing an active component of a hearing prosthesis against the mastoid bone, where and electrical lead extends from the housing to the inductance coil assembly. In this regard, this is consistent with the teachings detailed above with respect to utilizing the inductance coil to operate or otherwise energize the actuator of the bone conduction device or the stimulator of a cochlear implant, etc.

Figure 15:
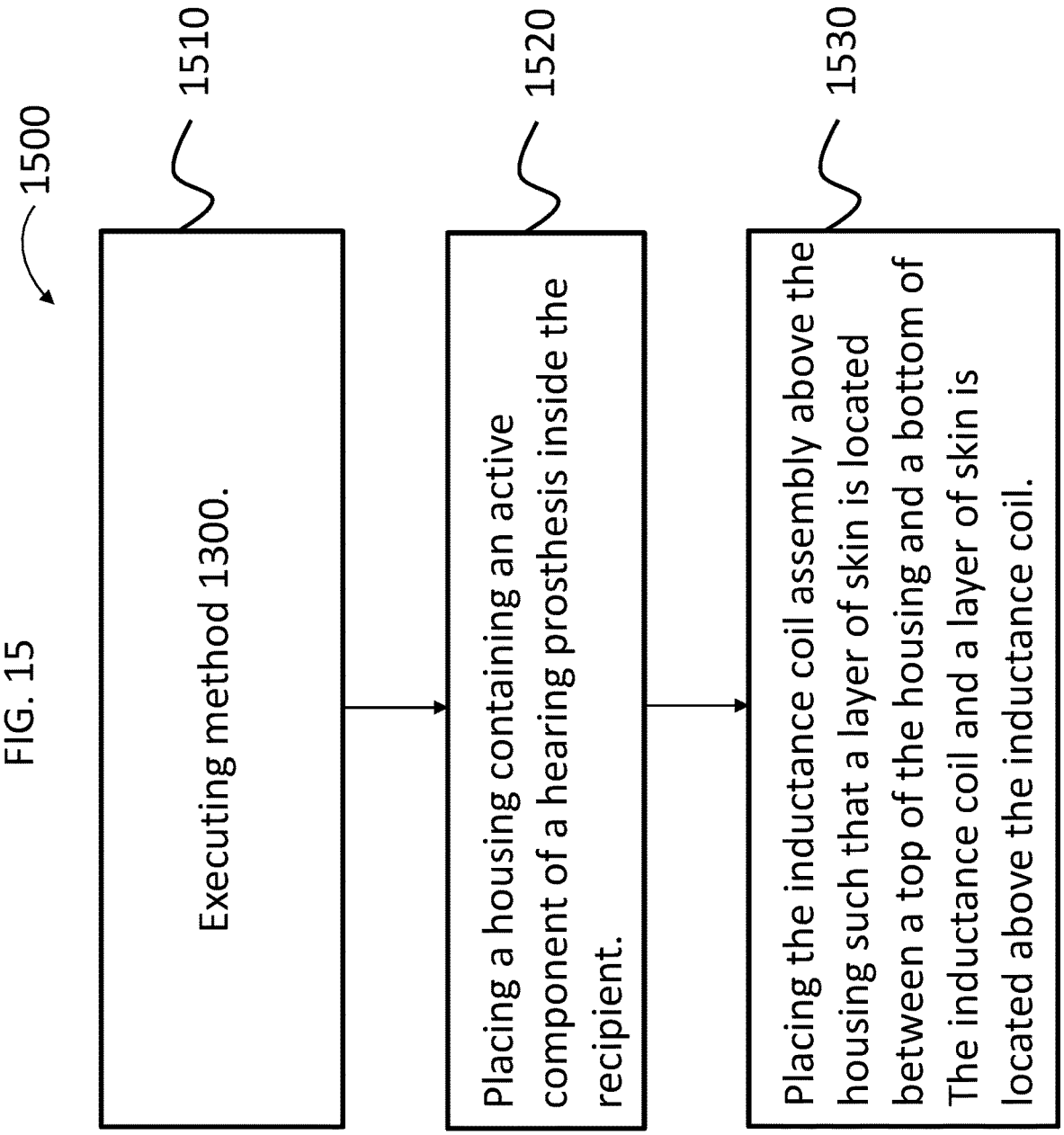
Figure 16:
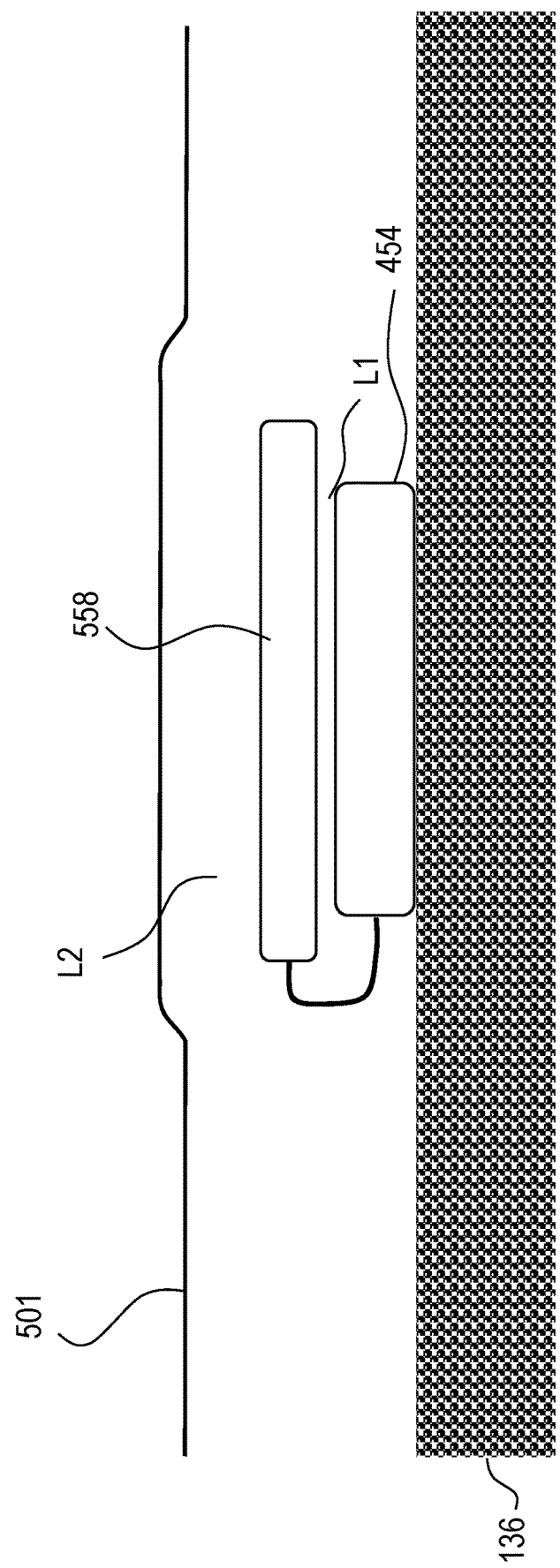
FIG. 16 depicts an alternate implantation arrangement of an implant according to an exemplary embodiment.

FIG. 15 presents another exemplary flowchart according to another exemplary method, method 1500, according to an exemplary embodiment. Method 1500 includes method action 1510, which includes executing method 1300. Method action 1520 of method 1500 includes placing a housing containing an active component of a hearing prosthesis inside the recipient. This can be done in any given manner, such as with respect to placing the housing against the bone of the recipient or placing the housing at an intracutaneous location (some additional details which will be described in greater detail below). Method 1500 further includes method action 1530, which includes placing the inductance coil assembly above the housing, the results of which are seen in FIG. 16. In this regard, method 1500 results in a layer of skin L1 being located between a top of the housing and a bottom of the inductance coil assembly, and a layer of skin L2 being located above the inductance coil assembly. In this exemplary embodiment, the active component located in the housing is in signal communication with the inductance coil assembly via an electrical lead extending from the housing to the inductance coil assembly.

Figure 17:
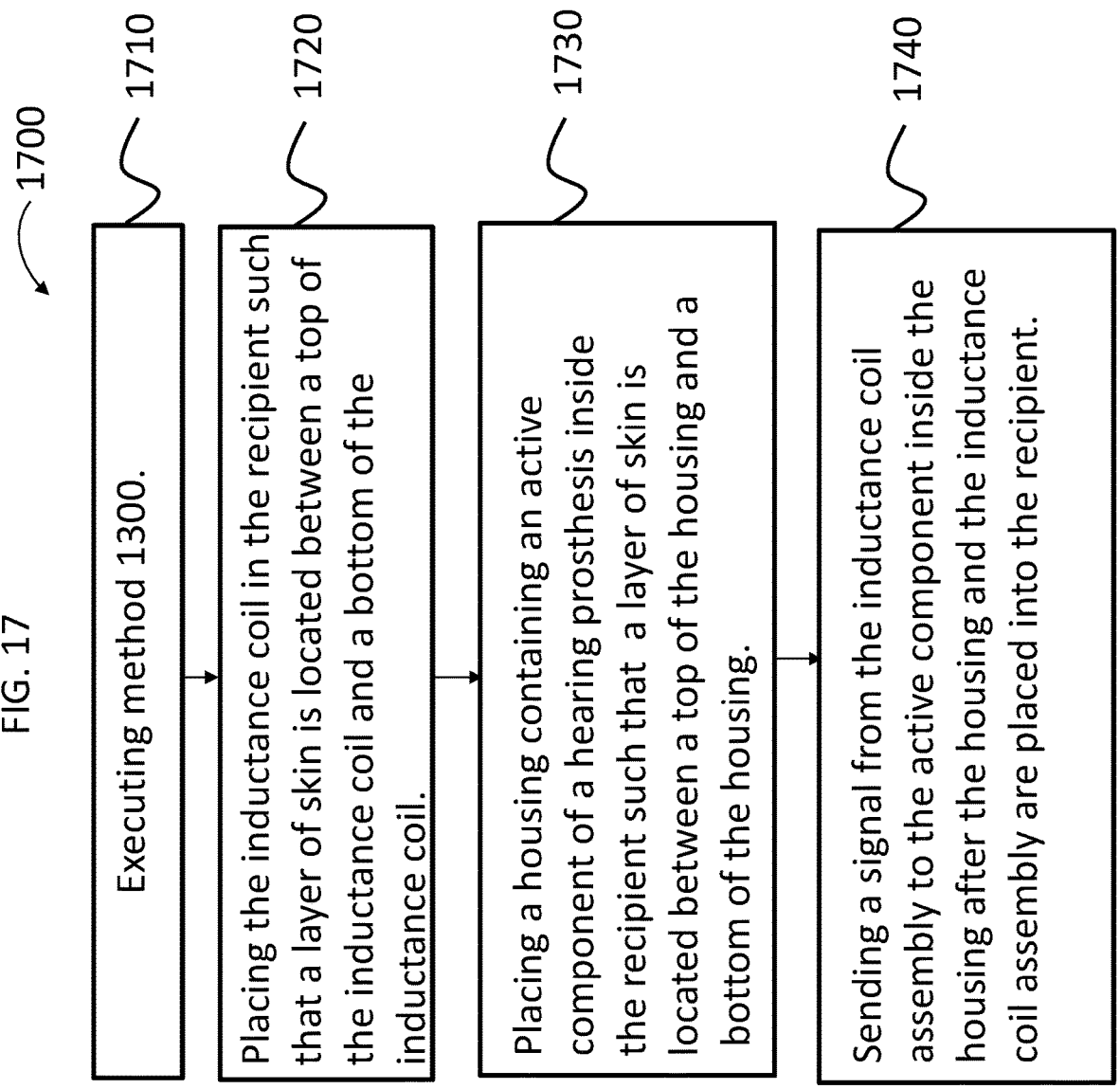
FIG. 17 represents a flowchart according to an exemplary method according to an exemplary embodiment.
Figure 18:
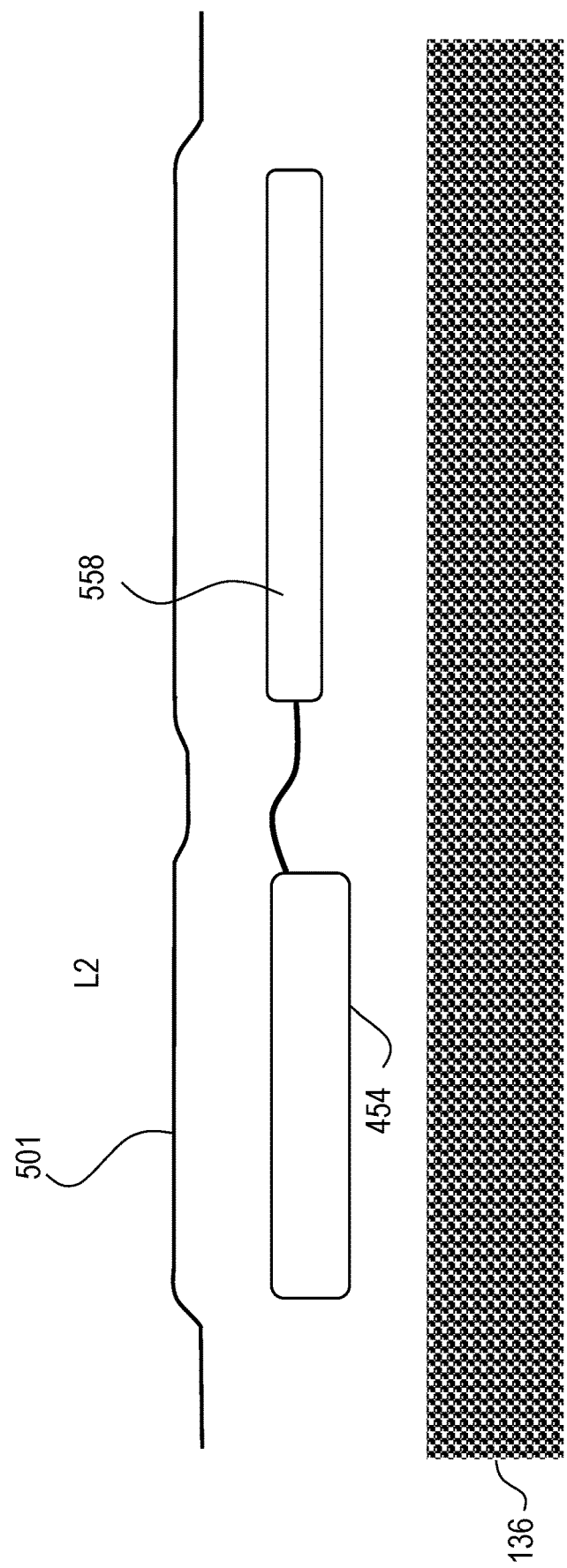
FIG. 18 depicts an alternate implantation arrangement of an implant according to an exemplary embodiment.

FIG. 17 presents another exemplary flowchart according to another exemplary method, method 1700. Method 1700 includes method action 1710, which includes executing method 1300. Method 1600 further includes method action 1720, which includes placing the inductance coil assembly in the recipient such that a layer of skin is located between a top of the inductance coil and the bottom of the inductance coil. With reference to FIG. 18, the results of action 1720 can be seen.

Method 1700 further includes method action 1730, which includes placing a housing containing an active component of a hearing prosthesis inside the recipient such that a layer of skin is located between a top of the housing and a bottom of the housing. The results of action 1730 can be seen in FIG. 18 as well. It is noted that the embodiment of FIG. 18 depicts the housing 454 being located at a different level within the skin of the recipient then the implanted receiver coil assembly 558. In an exemplary embodiment, the bottoms of those components can be aligned with each other (e.g., can have the same distance from the surface of bone 136 and/or from the surface of the skin 501) with the tops of those components can be aligned with each other, or a middle thereof can be aligned with each other. Any placement of the housing and the assembly corresponding to the features of method 1600 can be utilized in at least some exemplary embodiments.

Method 1700 further includes method action 1740, which include sending a signal from the inductance coil assembly 558 to the active component inside the housing 454 after the housing and the inductance coil assembly are placed into the recipient. In an exemplary embodiment, method action 1740 is executed by creating an inductance field utilizing an external coil located proximate the surface 501 of the skin, which inductance field is received transcutaneously by the coils of assembly 558. This inductance field induces a current in the coils of the assembly 558, which current is transferred via the lead to feedthrough is in the housing 454, and thus from the feedthroughs to the active component located in the housing 454. In an exemplary embodiment, as noted above, the active component can be a stimulator of a cochlear implant. In an exemplary embodiment, the active component can be an actuator of a bone conduction hearing prosthesis.

It is noted that while FIG. 18 depicts the implanted receiver coil assembly 558 as a separate component from the housing 454, it is noted that method 1700 can be executed utilizing an implantable component where the inductance coil assembly is not a distinct component relative to the assembly of which the stimulator is a part. In this regard, in an exemplary embodiment, the inductance coil assembly can be part of a so-called receiver-stimulator assembly of a cochlear implant, and the housing containing the active component can be a housing the stimulator of the cochlear implant, where a silicone body making up part of the implanted inductance coil assembly extends to envelop at least a portion of the housing that houses the stimulator of the cochlear implant. In such an exemplary embodiment, method actions 1720 and 1730 can be executed simultaneously or in an overlapping manner, etc.

It is noted that at least some exemplary embodiments include repeating method 1300, and, in some embodiments, some of the other methods detailed herein and/or variations thereof, repeatedly for a plurality of recipients. Accordingly, in an exemplary embodiment, there is a method that includes executing method 1300, method 1400, method 1500, and/or method 1700, and/or any of the other methods or method actions detailed herein and/or variations thereof at least X times for respectively different humans. Accordingly, in an exemplary embodiment, this can include executing method actions 1310 and 1320 at least X times. In an exemplary embodiment, X is 10, 15, 20, 25, 30, 35, 40, 45, 50, 55, 60, 65, 70, 75 or 80 or more. In an exemplary embodiment, this method is performed at least X times within a period less than 1 month, 2 months, 3 months, 4 months, 5 months, 6 months, 7 months, 8 months, 9 months, 10 months, 11 months, 12 months, 5 quarters (five 3 month periods), 6 quarters, 7 quarters, 8 quarters, 9 quarters, or less than 10 quarters.

In this exemplary embodiment of executing the various methods detailed herein, the inductance coil assembly is placed at respective first distances from an outer skin of the recipients, the respective first distances having respective values having differences there between no more than 0.25 mm, 0.33 mm, 0.5 mm, 0.66 mm, 0.75 mm, 1 mm, 1.25 mm, 1.5 mm, 1.75 mm, 2 mm, 2.25 mm, or 2.5 mm for the X number of different humans subjected to the method repeated X times. For example, if the differences therebetween are no more than 1 mm, that means that all of the X number of different humans will have the inductance coil assembly located, for example, within a range of 2 to 3 mm from the top surface, within a range of 1 to 2 mm from the top surface, within a range of 3 to 4 mm from the top surface, etc.

In an exemplary embodiment, at least some or all of the method actions detailed herein are executed without utilizing skin reduction. At least some of the exemplary embodiments detailed herein can enable such because the incision made within the skin to establish the pocket into which the implanted receiver coil assembly is located can be made a defined and control distance from the top surface of the skin. Thus, a desired distance from the top surface of the skin to the implanted receiver coil assembly can be controlled or otherwise established by measuring the distance from the top surface to the incision that will form the pocket. This as opposed to utilizing the skin reduction to remove skin that would be between the implanted receiver coil assembly and the outer surface of the skin to achieve a desired depth of the implanted receiver coil assembly from the outside surface of the skin. In this regard, in scenarios where the implanted receiver coil assembly was located directly on the bone of the recipient or directly on the mucous membrane covering the bone of the recipient, the thickness of skin covering the implanted receiver coil assembly might be such that less than utilitarian results would be achieved with respect to and inductance link extending from the implanted receiver coil assembly without skin reduction and the external inductance coil. Accordingly, there is utilitarian value with respect to utilizing skin reduction to thin the overlying skin over the implanted receiver coil assembly, and thus reduce the distance between the implanted receiver coil assembly in the outer surface of the skin and thus reducing the distance between the implanted receiver coil assembly and the external component containing the external coil assembly.

Figure 19:
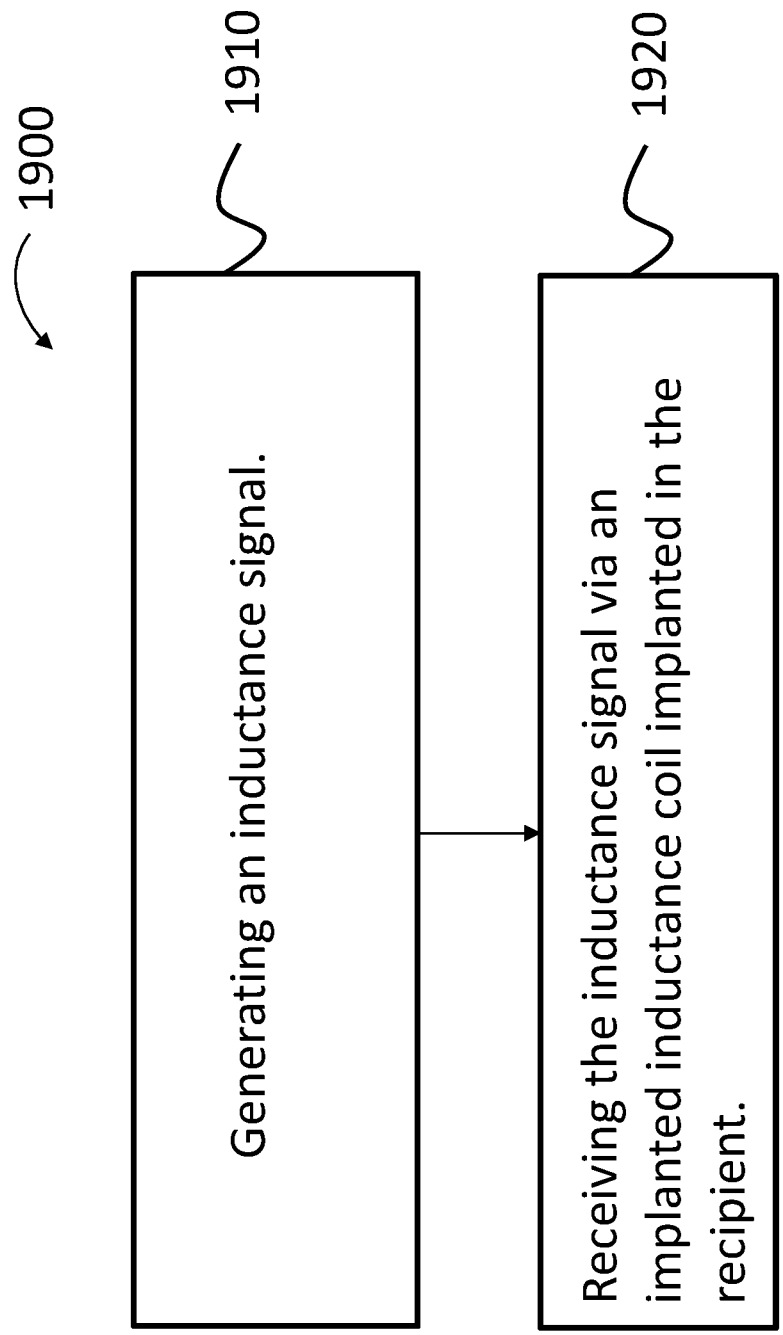
FIGS. 19 to 20 represent flowcharts according to some additional exemplary methods according to some exemplary embodiments.

FIG. 19 depicts another exemplary flowchart for an exemplary method, method 1900, according to an exemplary embodiment. Method 1900 is directed towards utilizing the implanted assembly implanted according to the method actions detailed above and/or utilizing the assembly having the configurations detailed above.

Method 1900 includes method action 1910, which includes generating and inductance signal. In an exemplary embodiment, method action 1910 is executed utilizing an external component of a hearing prosthesis that includes an external inductance coil. In an exemplary embodiment, the external component captures a sound utilizing a microphone, and, based on this captured sound, a current is applied to the external coil to generate an inductance field.

Method 1900 further includes method action 1920, which includes receiving the inductance signal via implanted inductance coil implanted in the recipient. In an exemplary embodiment, method action 1920 is executed utilizing the implanted receiver coil assembly 558 implanted according to the teachings detailed herein and/or variations thereof. In this method 1900, there is a layer of skin located between the inductance coil and the skull of the recipient in which the inductance coil is implanted, consistent with the teachings detailed herein.

In an exemplary embodiment of method 1900, the inductance coil, such as inductance coil 457, supported by an inductance coil support assembly, such as the silicon body in which the coil is embedded, which support assembly is completely away from the skull bones of the recipient, such as by way of example only and not by way of limitation, the mastoid bone of the recipient. It is noted that the support assembly is not to be confused with any other components that might support the entire assembly. In this regard, the inductance coil support assembly is just that, an assembly that supports the inductance coil (e.g., a housing, silicone body, etc.). In an exemplary embodiment, a support for the inductance coil support assembly can be utilized, which support assembly is separate from the inductance coil support assembly of this method.

Consistent with the embodiment of FIG. 16, in an exemplary embodiment of method 1900, the action of generating the inductance signal is executed utilizing an external inductance coil coaxially aligned with the implanted inductance coil. In an exemplary embodiment, this is achieved via the utilization of magnets having polls that are opposite one another. A first magnet is located in the external device and the external coil is wound thereabout (a given distance away from the magnet). In an exemplary embodiment, this first magnet is located such that the north or south pole of the magnet faces the skin of the recipient (although in other exemplary embodiments, the polls of the magnets are aligned horizontally with the skin of the recipient). A second magnet is located in the implanted receiver coil assembly and the implanted receiver coil is wound thereabout (again, a given distance away from the implanted magnet). In this exemplary embodiment, the polls of the second magnet are such that the pole facing the external magnet is the opposite of the pole of the external magnet facing the skin. Thus, the magnets saw the line, and the coils are generally coaxial with one another.

In an exemplary embodiment, method 1900 further includes the action of activating an active component of the hearing prosthesis, the active component being located in a housing, such as housing 454. In this exemplary method, the external inductance coil overlies the implanted inductance coil and the housing, and the implanted inductance coil overlies the housing. By "overlies," it is meant that when looking downward onto the skull of the recipient, and axis normal to the tangent plane of the skull at a particular location extends through the two components at issue. The components need not necessarily be completely overlapping one another as shown in FIG. 16. The components can be staggered. That said, in some other embodiments, all of the components are coaxially aligned and/or the component above completely overlaps the component below. That said, in an alternate embodiment, when viewed looking from the inside of the recipient outward, where, for example, the housing 454 would thus become the component above the implanted receiver coil assembly 558 with respect to FIG. 16, the component above completely overlaps the component below (this can be the case where housing 454 completely overlaps implanted receiver coil assembly 558, or implanted receiver coil assembly 558 completely overlaps the external coil assembly—both could be the case in some embodiments).

In view of the above, it can be understood that in an exemplary embodiment, there is an implanted receiver coil assembly, such as coil assembly 558, that is configured so as to not be placed directly on bone of the recipient. It can be further seen that in an exemplary embodiment, there is a coil assembly that is separated from the electronics of the implant in general, and the active component of the implant in particular.

Because in at least some exemplary embodiments the distance between the coil and the surface of the skin of the recipient is smaller than that which would otherwise be the case if the implanted receiver coil assembly was placed onto bone, at least not without skin thinning or the like, the coil can be optimized and/or otherwise made smaller than that which would otherwise be the case, all other things being equal. Still further, the fact that the distance is less than that which would otherwise be the case owing to the fact that the implanted receiver coil assembly is placed intracutaneously, at least without skin thinning, could result in a longer battery life of any battery powering the implanted components (whether that battery is external or internal to the recipient), a higher output of the device for a given input, and/or a smaller diameter of the coil of the implanted receiver coil assembly, all other things being equal. Again, in an exemplary embodiment, because the external and the implanted coil can be closer to each other than that which would otherwise be the case without the soft tissue mounting detailed herein, efficiency of the energy transfer over the skin can be improved. This gain in energy transfer could be utilized in several ways such as reduced size of the coils (one or both of the internal and external coils), increased output of the implanted component, or longer battery life for the external battery, etc.

It is also noted that in an exemplary embodiment, there are a plurality of separate inductance coil that are part of the implantable component. By way of example only and not by way of limitation, in an exemplary embodiment, a given housing containing an active component can have two separate inductance coils in signal communication therewith. In an exemplary embodiment, one of the inductance coils is located intracutaneously within the recipient, and another one of the coils is located subcutaneously above the skull of the recipient (i.e., the second coil is not located intracutaneously within the recipient/the second coil is located non-intracutaneously).

Figure 20:
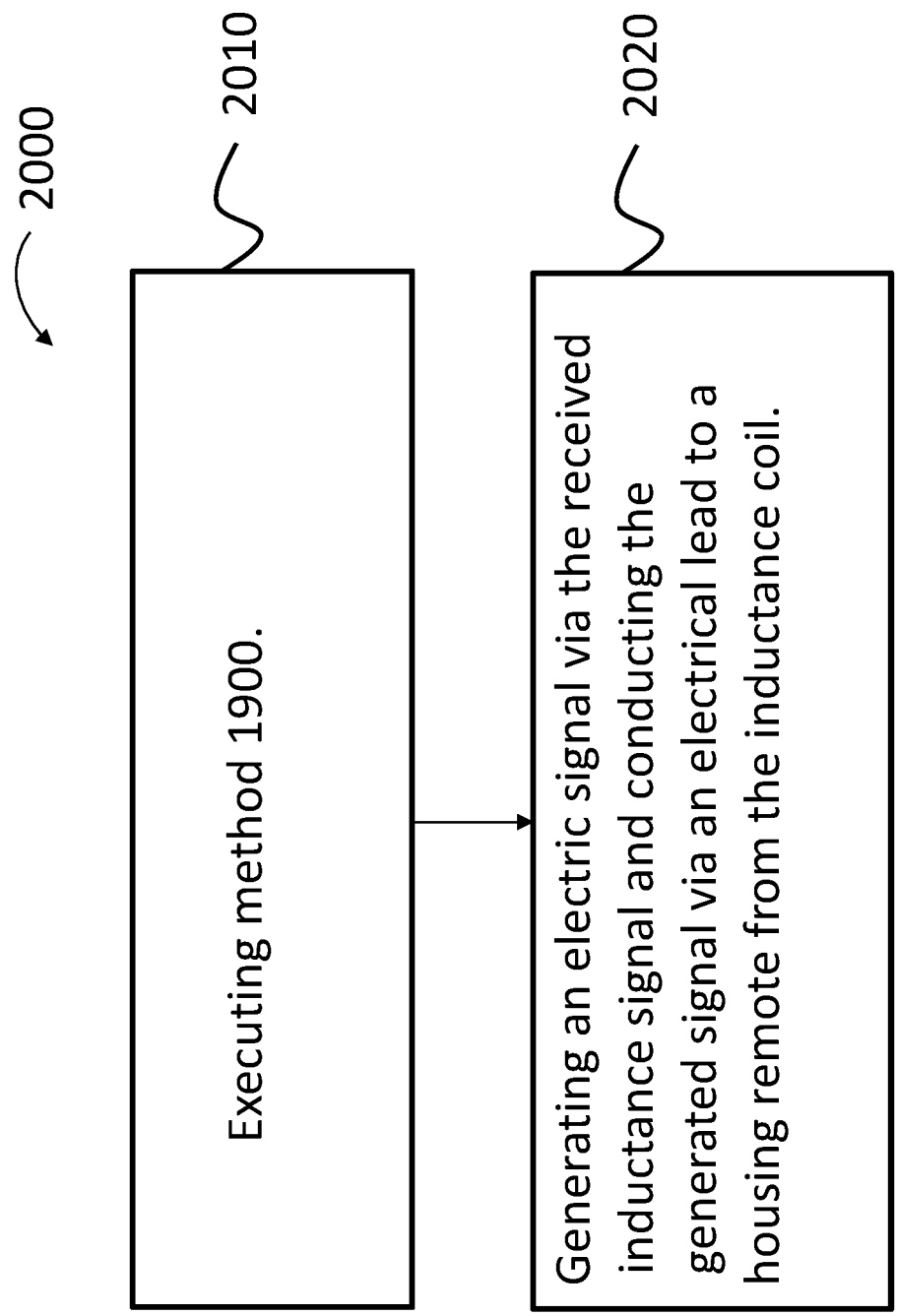

FIG. 20 depicts another exemplary flowchart for an exemplary method, method 2000, which includes method action 2010, which includes executing method 1900. Method 2000 further includes method action 2020, which includes generating an electric signal via the received inductance signal received in method action 1920, and conducting the generated signal via an electrical lead to a housing remote from the inductance coil utilized in method action 1920. In this exemplary embodiment, the electrical lead hold the inductance coil in position relative to the housing. In an exemplary embodiment includes a semi-rigid lead that is malleable by hand or the like but is rigid enough so as to hold the implanted receiver coil assembly 558 in position relative to the housing to which it is attached.

More particularly, in an exemplary embodiment, the lead extending from the implanted receiver coil assembly 558 to the housing 454 includes a device configured to prevent, or at least resist, movement of at least a portion of the lead assembly in a manner greater than that with respect to conventional leads. More specifically, in an exemplary embodiment, there can be a lead assembly including a device that is configured to resist movement of at least a portion of the lead assembly, and thus the implanted receiver coil assembly. In an exemplary embodiment, the movement is resisted or otherwise prevented from occurring due to a structure co-located with the lead assembly. In an exemplary embodiment, this entails a malleable portion, co-located with the leads in the lead assembly. That said, in another exemplary embodiment, the malleable portion can be the lead wires themselves, where, for example, the lead wires are made thicker than that which would normally be the case so as to establish the aforementioned rigidity/malleability so as to maintain the position of the implanted receiver coil assembly in place at least relative to that which would be the case in the absence of such lead assembly (e.g., where a normal lead assembly was utilized).

In an exemplary embodiment, there is a lead assembly that includes a malleable metal wire, embedded in the body establishing the lead assembly. In an exemplary embodiment, the wire leads of the lead assembly are embedded in silicone, which establishes the body of the lead assembly. A malleable wire can be embedded in the silicone body of the lead assembly.

In an exemplary embodiment, the metal wire is made of platinum or some other "soft" metal. That said, in some embodiments, depending on the dimensions, a stainless steel or the like could be used (providing that the diameter was thin enough to enable the bending having utilitarian value detailed herein). Other metals and alloys can be utilized. Any metal and/or alloy that is malleable in a given structural configuration that can enable the teachings detailed herein and/or variations thereof to be practiced can be utilized in at least some embodiments. Other types of material can be utilized as well, such as by way of example only and not by way of limitation, a plastically deformable polymer, again providing that the teachings detailed herein and/or variations thereof can be practiced.

In some embodiments, this malleable wire providing the aforementioned rigidity is not utilized to conduct signals, while in other embodiments, the malleable wire is utilized to conduct signals. In an exemplary embodiment, the diameter of the malleable structures utilized to achieve the aforementioned positioning of the implanted receiver coil assembly have a diameter that is an order of magnitude larger than that of a given lead wire of the lead assembly.

To be clear, these embodiments are not to be confused with the mere fact that a lead assembly exists that limits the distance that the implanted receiver coil assembly might travel from the housing 454 owing to the fact that the lead has a finite length. That is not positioning. That is captivity.

Accordingly, in an exemplary embodiment, there is an implant that is configured to provide for a defined placement of the receiver coil assembly relative to a surface of the skin. As detailed above, in this exemplary embodiment, such is achieved utilizing the enhanced lead assembly according to the teachings detailed herein and/or variations thereof.

Figure 21:
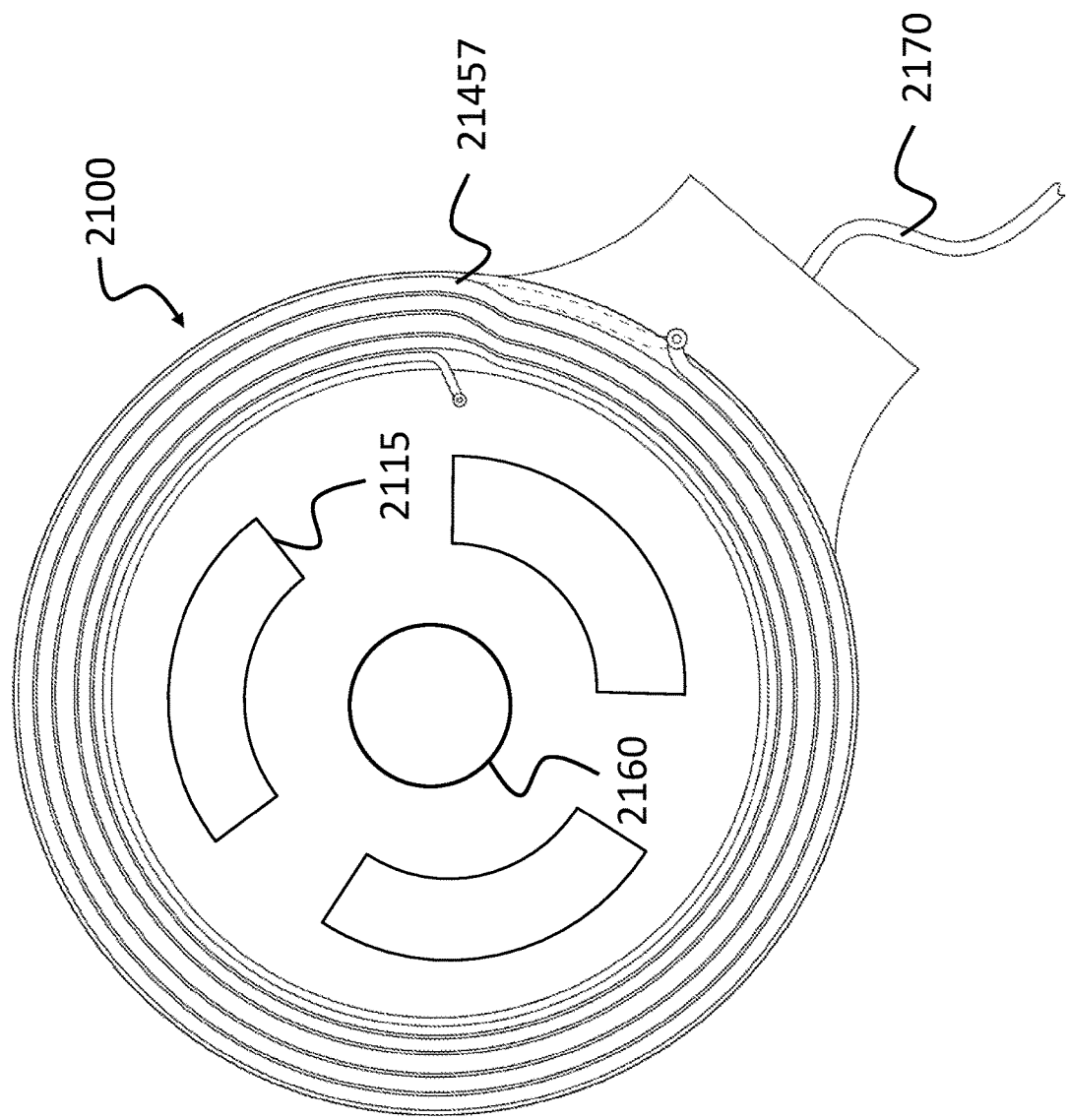
FIG. 21 depicts an exemplary implanted receiver coil assembly according to an exemplary embodiment.

FIG. 21 provides for another exemplary embodiment for providing for defined placement of the assembly relative a surface of the skin. In particular, there is an implantable receiver coil assembly 2100 depicted, the assembly being attached to lead 2170. In an exemplary embodiment, the lead 2170 can include the features detailed above vis-à-vis the stiffening feature. In an exemplary embodiment, the lead 2170 is a non-stiffened lead. In any event, implanted assembly 2100 includes holes 2115 that extend completely from a top of the implanted receiver coil assembly 2100 to the bottom of the assembly 2100 so as to enable can growth therethrough (e.g. from the top to the bottom, from the bottom to the top, and were from the top and bottom meeting somewhere in between). (Note some elements are not present for reasons of clarity.)

As can be seen, holes 2115 are inboard of the coils 21457 and outboard of the magnet 2160. In an exemplary embodiment, holes 2115 through the silicon body are holes that holds the coils 21457 in place. That said, in an alternate embodiment, such as where the coils 21457 are traces on a PCB or the like, instead of wires held in space via a silicon body, holes 2115 can extend through the PCB. In an exemplary embodiment where the coils 21457 are located in a housing or the like, holes 2115 can extend from the top of the housing to the bottom of the housing. In some exemplary embodiments, the housing is such that the holes are formed by extensions of the housing walls inward towards each other so as to create a hermetic environment within the housing at the locations on the other side of the extender walls. That is, holes 2115 do not interfere with the purposes of the housing these are the protecting what is in the housing from the external environment of the housing.

While three holes are depicted in the embodiment of FIG. 21, in some alternate embodiments, only one hole is utilized. In some other embodiments, two holes are utilized. In some embodiments, four or more holes are utilized. It is also noted that while the embodiment depicted in FIG. 21 utilizes holes that are generally the same as one another and symmetrically arrayed relative to one another, in an alternate embodiment, the holes can be different from one another and are not symmetrically arrayed. Also, while the holes are depicted inboard of the coils 21457, in an alternate embodiment, one or more of the holes can be located outboard of the coils. Any arrangement that can enable the teachings detailed herein can be practiced in at least some exemplary embodiments.

It is also noted that in an exemplary embodiment, other features that can enhance the locational stability of the implantable receiver coil assembly 2100 can be utilized. By way of example only and not by way of limitation, instead of through holes that extend completely through the assembly, in an alternate embodiment, hollows or divits can be utilized. Still further, in an exemplary embodiment, spikes can be utilized. Surface features can be provided that enhance the locational positioning, such as by way of example only and not by way of limitation, a roughened surface. Still further, in an exemplary embodiment, the surface of the implantable receiver coil assembly can include some form of compound that enhances adherence to skin. In some embodiments, the surface of the implantable receiver coil assembly can be coated with a material that enhances such adherence to skin. In an exemplary embodiment, a gridlike structure can be placed on one or both sides of the implantable receiver coil assembly, which gridlike structure is configured so as to enhance skin in-growth and the like. Any arrangement that can further enhance the locational stability of the implantable receiver coil assembly 2100 can be utilized. Is also noted that any of the aforementioned features can be utilized in combination with any of the other aforementioned features.

In at least some exemplary embodiments, the holes 2115 are configured such that skin or other soft tissue (herein, any disclosure of skin also corresponds to a disclosure of other types of soft tissue, and vice versa—this does not mean that skin has been equated to any type of soft tissue, this simply means that for the purposes of linguistic economy, Applicant intends for the disclosure of skin to also correspond to the disclosure of other types of soft tissue for purposes of written description support for the latter) grows into the holes, thus providing for defined placement of the assembly relative to the surface of the skin.

Accordingly, in an exemplary embodiment of method 1900, method 1900 is executed where skin is ingrown into an assembly including the inductance coil, the skin extending from a first side of the inductance coil to a second side of the inductance coil, thereby preventing the coil from migrating within the skin of the recipient, or at least substantially limiting the ability of the coil from migrating within the skin of the recipient, at least relative to that which would be the case in the absence of the holes 2115.

It is further noted that the aforementioned stiffened lead can also provide utility with respect to preventing or at least substantially limiting the ability of the coil from migrating within the skin of the recipient.

That said, in some alternative embodiments, the holes may not necessarily prevent or otherwise limit migration. Instead, the holes are utilized to stabilize the implanted receiver coil assembly. Accordingly, in an exemplary embodiment, the holes are configured for soft tissue of the recipient to grow therethrough so as to stabilize the implanted receiver coil assembly 558.

Figure 22:
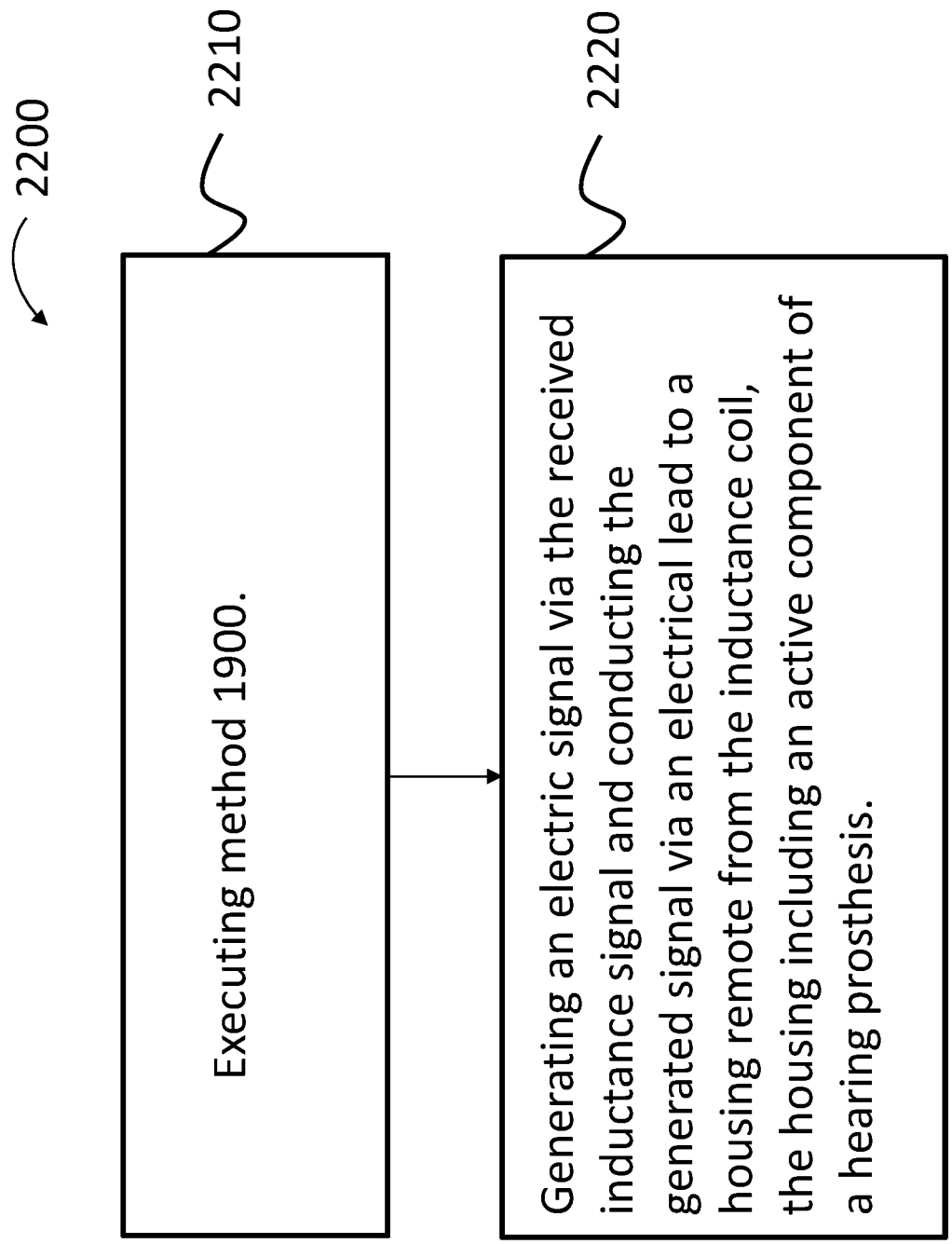
FIG. 22 represents an exemplary flowchart according to an exemplary method according to an exemplary embodiment.

With reference back to FIG. 18 and the housing 454 that is located intracutaneously, along with reference back to FIG. 16, for example, where the housing 454 is located subcutaneously, in an exemplary embodiment, there is a method represented by the flowchart of FIG. 22. More particularly, there is a method 2200, which includes method action 2210, which includes executing method 1900. Method 2200 further includes method action 2220, which includes generating an electric signal via the received inductance signal received in method 1900, and conducting the generated signal via an electrical lead to a housing remote from the inductance coil (the inductance coil utilized to execute method 1900). In this exemplary method, the housing includes an active component of a hearing prosthesis. In this exemplary method, this housing is one of (i) retained to the skull only via osseointegration, (ii) retained to the skull only via pressure of skin over the top of the housing or (iii) not in contact with the skull or periosteum. That is, in some embodiments, the housing that contains the active component does not include a bone screw or the like to hold the housing in place.

To be clear, in an exemplary embodiment, the implant is drill-hole and/or screw hole free, or more accurately, the implant is implanted without drilling and/or without screwing into bone. In an exemplary embodiment, at least the bottom of the housing can have a surface that is structured or otherwise coated so as to stimulate or otherwise encourage osseointegration to bone of the recipient. That said, in some alternate embodiments, the surface of the housing, or at least the bottom of the housing, is structured or otherwise coated so as to prevent or otherwise discourage osseointegration to bone of the recipient.

As noted above, some exemplary embodiments include a tool that is utilized to make the incision 620 that forms the pocket into which the implanted receiver coil assembly 558 is inserted. In this regard, FIGS. 23 and 24 depict such a tool.

Figure 23:
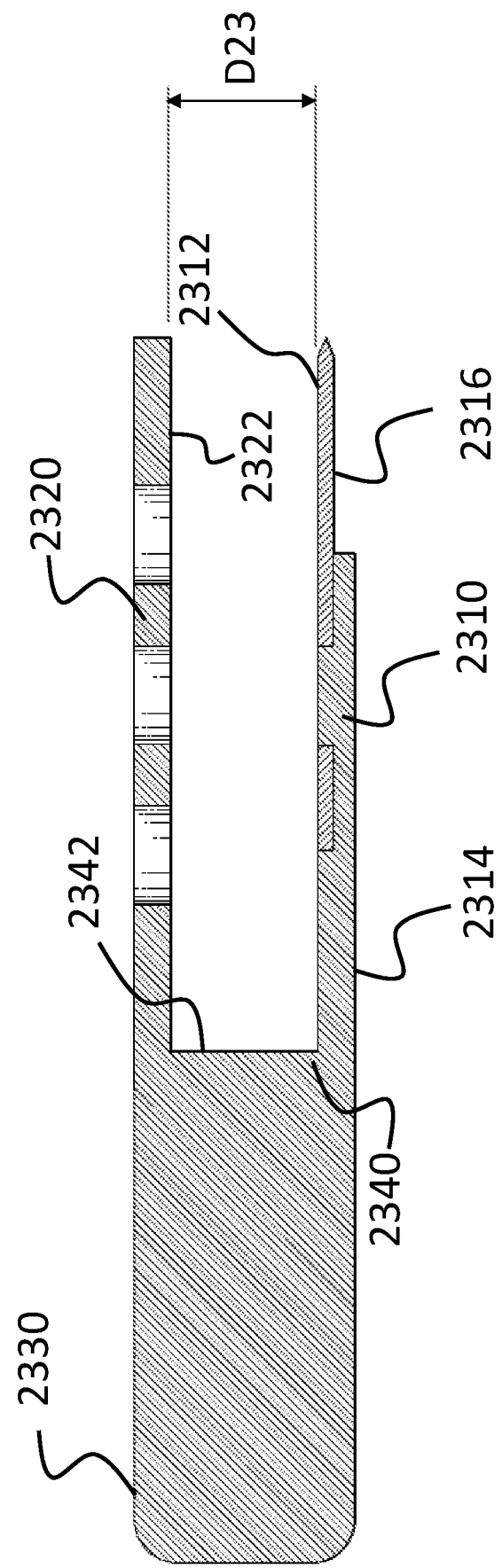
FIGS. 23 and 24 depict an exemplary hand tool according to an exemplary embodiment.
Figure 24:
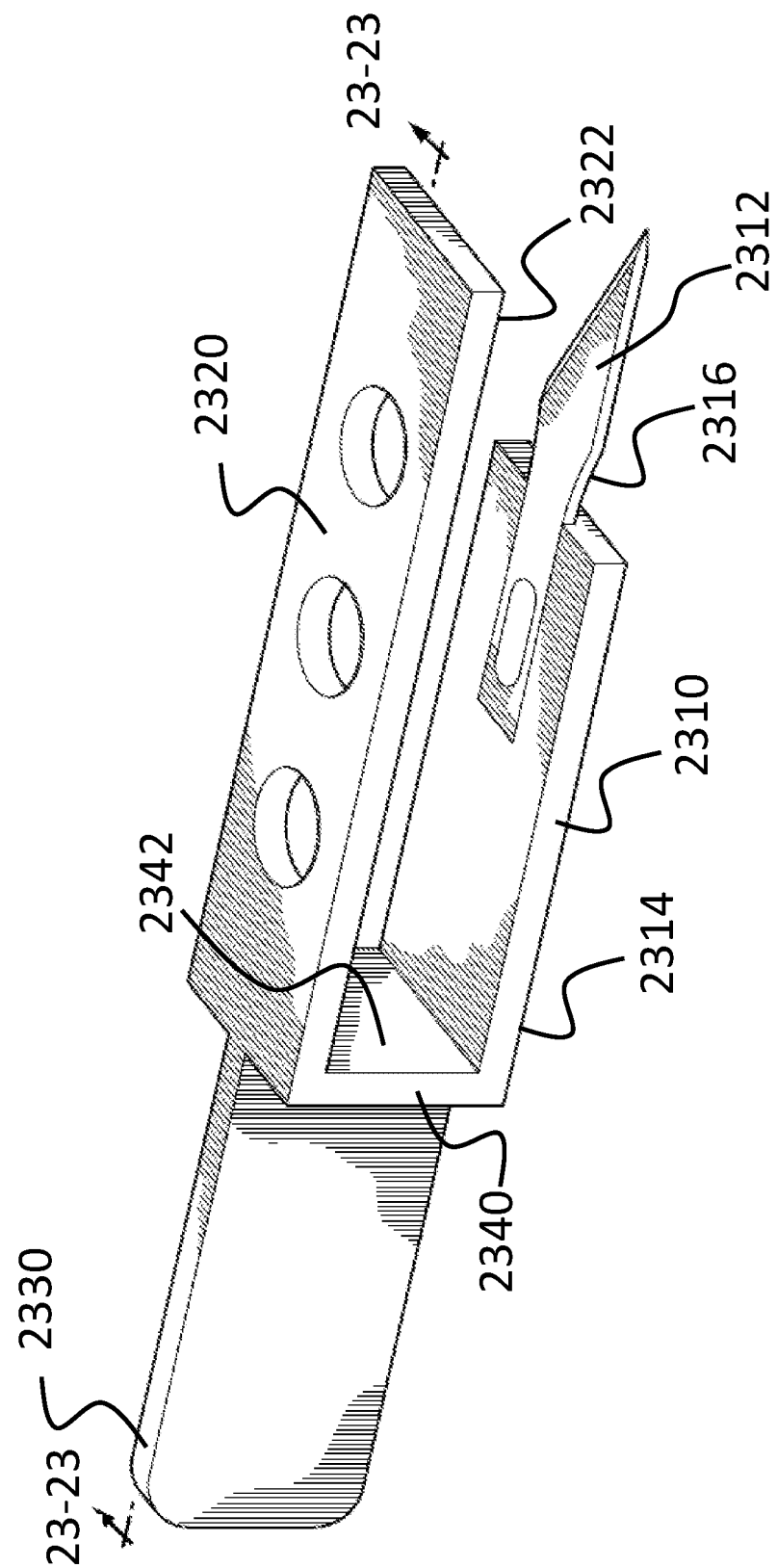

More particularly, FIGS. 23 and 24 depict a device, comprising a first portion 2310 that includes a first surface 2312. In an exemplary embodiment, the portion 2310 is a composite of a plate component 2314 to which is attached a scalpel blade 2316. In this regard, in an exemplary embodiment, the device depicted in FIGS. 23 and 24 is a soft-tissue gauge, such as that marketed and otherwise distributed by Cochlear Limited LTD, to which is attached a scalpel blade 2316. Additional details of such are described in greater detail below. In any event, according to the embodiment of FIGS. 23 and 24, the first surface is part of a scalpel blade.

The device of FIGS. 23 and 24 further includes a second portion 2320 including a second surface 2322 a fixed distance D23 from the first surface. The second surface 2322 is parallel to the first surface and overlying the first surface when the surfaces are positioned perpendicular to the direction of gravity (e.g., downward with respect to the frame of reference of FIG. 23).

The first portions of the second portions are joined together by third portion 2340 which extends in a perpendicular direction to the first and second portion. With respect to the exemplary embodiment of FIG. 23, other than the scalpel blade 2316, the first portion, the second portion of the third portion are part of a monolithic component in the form of a plate that has been bent over upon itself as can be seen. The third portion includes a surface 2342 which corresponds to the stop noted above with respect to the exemplary method of creating the pocket utilizing the tool described above. In this regard, in an exemplary embodiment, the stop 2342, during use, strikes the inside wall of the incision 610 on the side facing the pocket so as to prevent the device in general, and the tip of the scalpel blade 2316 in particular, from traveling further therein. That is, the stop 2342 establishes the length and/or the width of the pocket, and provides that no more cutting into the skin in the direction parallel to the surface of the skin is performed than that needed. As can be seen from the figures, the first portion, the second portion and the third portion collectively form a U-shaped component when viewed from the side (the view of FIG. 23).

The device in FIGS. 23 and 24 further include a handle 2330. This is utilized by the surgeon or other healthcare professional so as to allow for ease of manipulation of the device during the incision process creating the pocket into which the implanted receiver coil assembly 558 is inserted.

In the embodiments of FIGS. 23 and 24, the second surface 2322 is configured to about an outside of the skin, such as surface 501, of a human, where the skin is over the mastoid bone of the human. Still further, the first surface is configured to incise the pocket 620 in skin of the human over the mastoid bone such that the pocket has a constant distance from the outside of the skin of the human. In the exemplary embodiment depicted in FIGS. 23 and 24, this is due to the second surface 2322 and the fact that the first surface 2312 is rigidly connected indirectly to the second surface 2322 via the structure of the device.

The distance D23 is a set distance of the manufactured tool. In an exemplary embodiment, D23 can correspond to any of the dimensions D1 or D3 noted above. Indeed, in an exemplary embodiment, the distance D23 establishes D1 or D3. To be clear, in the embodiment depicted in the figures, the first surface and the second surface are separated by a distance of D23.

As noted above, the device can be a soft-tissue gauge or a modified soft-tissue gauge to which a scalpel blade has been attached. By way of example only and not by way of limitation, a recess can be formed in the upper surface of the plate that forms the portion 2310 so that the scalpel blade 2316, or, more accurately, the bank of the scalpel blade 2316, can be recessed such that the top surface of the scalpel blade is parallel with the top surface of the plate that forms the portion 2310. That said, in an alternate embodiment, the scalpel blade can be located proud of the top surface that forms the plate. In this regard, if for example, a pocket located 4 mm below the outside surface of the skin is desired, a skin thickness gauge of 4.25 mm might be utilized, where the thickness of the scalpel blade is about 0.25 mm. Any arrangement that can enable the teachings detailed herein and/or variations thereof can be utilized in at least some exemplary embodiments.

Owing to the fact that the surface 2322 is configured to be placed against the outside surface 501 of the skin, the device of FIGS. 23 and 24 is thus configured to cut respective pockets in skin of a human parallel to the skull bone of the human a constant depth from a surface of the skin when the second surface is positioned against the outside of the skin.

In view of the above, in an exemplary embodiment, method 1300 includes the additional action of utilizing a tool, such as the tool of FIGS. 23 and 24, to a button outside of the skin of the human to cut into the skin of the human to form an intracutaneous pocket in the skin while the tool is abutting the outside of the skin. In this exemplary embodiment, the tool maintains a uniform depth of the cut pocket relative to the outside of the skin due to the abutting of the outside of the skin.

In an exemplary embodiment, the tool can have markings thereon that provide a visual indication to the surgeon or other health care professional as to where a portion of the blade is located (which is eclipsed by the skin during normal use). For example, the tool could have an indication above the tip of the blade, indicating to the surgeon the location of the blade. For example, an outline of the blade can be located on 2320. Indeed, a cut-out in 2320 could be present that would correspond to the shape of the blade beneath. Alternatively, 2320 could be a transparent material, with an outline of the blade (or a schematic having even more details, such as the tapered portion of the blade as well) stenciled on the transparent portion. These latter embodiments could give the surgeon a visual cue of where the blade is located when the surgeon is looking downward directly from the top. The tool could have markings indicating the actual (lateral) depth of the cut or markings corresponding to recommended incision depths, etc.

Corollary to this is that in an exemplary embodiment, there is a method, comprising cutting a generally vertical incision into skin of the recipient extending towards bone of the recipient. In an exemplary embodiment, the incision corresponds to incision 610 detailed above. It is noted that this does not mean that the incision extends all the way to the bone. All that is required by this method action is that the incision extend towards the bone of the recipient. It is also noted that while this embodiment references a generally vertical incision, in some other embodiments, the incision need not necessarily be vertical relative to the bone. It is also noted that this vertical incision, as detailed above, is art unit when viewed looking downward from the outside of the skin. This method further includes the action of cutting a pocket perpendicular to the generally vertical incision utilizing the device of FIGS. 23 and 24. In an exemplary embodiment, this method includes inserting an inductance coil assembly according to the teachings detailed herein into the formed pocket.

In an exemplary embodiment, there is a method as described above and/or below, further comprising executing the method actions of cutting into skin of the human and placing the inductance coil above the mastoid bone through the cut at least 25 times for respectively different humans, wherein respective top surfaces of the inductance coil assemblies are placed respective first distances from an outer skin of the recipients, the respective first distances having respective values having differences therebetween no more than 1 millimeter for the 25 different humans.

In an exemplary embodiment, there is a method as described above and/or below, further comprising executing the method actions of cutting into skin of the human and placing the inductance coil above the mastoid bone through the cut at least 25 times for respectively different humans without using skin reduction, the inductance coil is placed respective first distances from an outer skin of the recipients, the respective first distances having respective values having differences therebetween no more than 1 millimeter for the 25 different humans.

In an exemplary embodiment, there is a device as describe above and/or below, wherein the first surface and the second surface are separated by a distance of between 3 mm and 5 mm.

It is noted that any disclosure of a device and/or system herein corresponds to a disclosure of a method of utilizing such device and/or system. It is further noted that any disclosure of a device and/or system herein corresponds to a disclosure of a method of manufacturing such device and/or system. It is further noted that any disclosure of a method action detailed herein corresponds to a disclosure of a device and/or system for executing that method action/a device and/or system having such functionality corresponding to the method action. It is also noted that any disclosure of a functionality of a device herein corresponds to a method including a method action corresponding to such functionality. Also, any disclosure of any manufacturing methods detailed herein corresponds to a disclosure of a device and/or system resulting from such manufacturing methods and/or a disclosure of a method of utilizing the resulting device and/or system.

Unless otherwise specified or otherwise not enabled by the art, any one or more teachings detailed herein with respect to one embodiment can be combined with one or more teachings of any other teaching detailed herein with respect to other embodiments.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

In view of FIG. 3, embodiments include a method, comprising cutting into skin of a human recipient above a temporal bone of the recipient and placing an inductance coil assembly subcutaneously above the mastoid bone through the cut into the skin, wherein placing the inductance coil assembly subcutaneously above the mastoid bone through the cut into the skin is executed by placing the inductance coil assembly non-intracutaneously above the mastoid bone through the cut into the skin and/or placing the inductance coil assembly non-intracutaneously above the mastoid bone through the cut into the skin includes placing the inductance coil assembly directly against the mastoid bone at a location above an ear canal relative to a height of a human into which the inductance coil assembly is being placed, wherein the sensory implant is a cochlear implant.

What is claimed is:

1. A method, comprising:
   cutting into skin of a human recipient above a temporal bone of the recipient; and
   placing an inductance coil assembly intracutaneously above the mastoid bone through the cut into the skin.

2. The method of claim 1, wherein:
   the action of placing the inductance coil assembly intracutaneously above the mastoid bone results in the inductance coil being located such that there is between about 2 mm and about 5 mm of skin above the inductance coil assembly and at least about 1 mm of skin below the inductance coil assembly.

3. The method of claim 1, wherein:
   the action of placing the inductance coil assembly intracutaneously above the mastoid bone results in the inductance coil assembly being located such that there is between about 3.5 mm and about 4.5 mm of skin above the inductance coil assembly and at least about 1 mm of skin below the inductance coil assembly.

4. The method of claim 1, wherein:
   the action of cutting into the skin of the recipient includes cutting a pocket into the skin, the pocket having a width and a length that extends at least generally parallel to a surface of the mastoid bone above the recipient.

5. The method of claim 1, further comprising:
   placing a housing containing an active component of a hearing prosthesis against the mastoid bone, wherein an electrical lead extends from the housing to the inductance coil assembly.

6. The method of claim 1, further comprising:
placing a housing containing an active component of a hearing prosthesis inside the recipient and;
placing the inductance coil assembly above the housing such that a layer of skin is located between a top of the housing and a bottom of the inductance coil assembly and a layer of skin is located above the inductance coil assembly, wherein
the active component is in signal communication with the inductance coil assembly via an electrical lead extending from the housing to the inductance coil assembly.

7. The method of claim 1, further comprising:
placing the inductance coil assembly in the recipient such that a layer of skin is located between a top of the inductance coil and a bottom of the inductance coil; and
placing a housing containing an active component of a hearing prosthesis inside the recipient such that a layer of skin is located between a top of the housing and a bottom of the housing, and
sending a signal from the inductance coil assembly to the active component inside the housing after the housing and the inductance coil assembly are placed into the recipient.

8. The method of claim 1, further comprising:
utilizing a tool configured to abut an outside of the skin of the human to cut into the skin of the human to form an intracutaneous pocket in the skin, wherein the tool maintains a uniform depth of the cut pocket relative to the outside of the skin.

9. The method of claim 1, wherein:
the method is executed using a device comprising a first portion including first surface and a second portion including a second surface a fixed distance from the first surface, the second surface is parallel to the first surface and overlies the first surface when the surfaces are positioned perpendicular to the direction of gravity, wherein the first surface is part of a scalpel blade.

10. The method of claim 9, wherein:
the first portion is part of a soft tissue gauge to which the scalpel blade has been attached.

11. The method of claim 9, wherein:
the first portion and the second portion are connected together and held apart by a third portion, the first portion, the second portion and the third portion combined forming a U shaped component when viewed from the side.

12. The method of claim 9, wherein:
the device is configured to cut respective pockets in skin of a human parallel to a skull bone of the human a constant depth from a surface of the skin when the second surface is positioned against the outside of the skin.

13. The method of claim 1, wherein the method further comprises:
incising a pocket in the skin over the mastoid bone such that the pocket has a constant distance from the outside of the skin of the human using a tool that has a surface that is configured to abut an outside of the skin over the mastoid bone and is abutting the outside of the skin over the mastoid bone during the action of incising.

14. The method of claim 1, further comprising:
executing the method actions of cutting into skin of the human and placing the inductance coil above the mastoid bone through the cut at least 25 times for respectively different humans, wherein respective top surfaces of the inductance coil assemblies are placed respective first distances from an outer skin of the recipients, the respective first distances having respective values having differences therebetween no more than 1 millimeter for the 25 different humans.

15. The method of claim 1, further comprising:
executing the method actions of cutting into skin of the human and placing the inductance coil above the mastoid bone through the cut at least 25 times for respectively different humans without using skin reduction, the inductance coil is placed respective first distances from an outer skin of the recipients, the respective first distances having respective values having differences therebetween no more than 1 millimeter for the 25 different humans.

16. The method of claim 1, wherein:
the action of cutting into the skin includes cutting a generally vertical incision into the skin extending towards the mastoid bone of the recipient and cutting a pocket perpendicular to the generally vertical incision.

17. The method of claim 16, further comprising:
inserting the inductance coil assembly into the pocket.

18. The method of claim 1, wherein:
the action of placing the inductance coil assembly results in the assembly being placed in soft tissue of the recipient.

19. The method of claim 1, wherein:
the assembly includes holes extending all the way therethrough from an upper surface to a lower surface of the assembly.

20. The method of claim 19, wherein:
the holes are configured for soft tissue of the recipient to grow therethrough so as to stabilize the assembly.

21. The method of claim 1, wherein:
a lead assembly extends from the assembly, wherein the lead assembly is a malleable.

22. The method of claim 1, wherein:
the inductance coil assembly is part of an implant that includes an active component of a hearing prosthesis located in a housing remote from the assembly, wherein the assembly is in signal communication with at least one component located in the housing via a lead extending from the assembly to the housing.

23. The method of claim 1, wherein:
the inductance coil assembly is part of an implant that includes an electro-mechanical transducer located in a housing remote from the assembly, wherein the assembly is in signal communication with at least one component located in the housing via a lead extending from the assembly to the housing.

24. The method of claim 1, wherein:
the inductance coil assembly is part of an implant that is configured to provide for defined placement of the assembly relative to a surface of the skin.

25. The method of claim 1, further comprising:
generating an inductance signal external to the recipient; and
receiving the inductance signal via the inductance coil assembly located at the position after the placement thereof intracutaneously above the mastoid bone through the cut into the skin in the recipient, wherein a layer of the skin is located between the inductance coil assembly and the mastoid bone.

26. The method of claim 25, further comprising:
generating an electric signal via the received inductance signal and conducting the generated signal via an electrical lead to a housing remote from the inductance coil assembly, wherein the electrical lead holds the inductance coil assembly in position relative to the housing.

27. A method, comprising:

generating an inductance signal external to a recipient; and receiving the inductance signal via an implanted inductance coil implanted in the recipient, wherein a layer of skin is located between the inductance coil and a skull a recipient in which the inductance coil is implanted.

28. The method of claim 27, wherein:

skin has ingrown into an assembly including the inductance coil, the skin extending from a first side of the inductance coil to a second side of the inductance coil, thereby preventing the coil from migrating within the skin of the recipient.

\* \* \* \* \*